United States Patent
Yoshida et al.

(10) Patent No.: US 6,566,671 B1
(45) Date of Patent: May 20, 2003

(54) MICROSCOPIC DEFECT INSPECTION APPARATUS AND METHOD THEREOF, AS WELL AS POSITIONAL SHIFT CALCULATION CIRCUIT THEREFOR

(75) Inventors: Atsushi Yoshida, Toyohashi; Shunji Maeda, Yokohama; Takafumi Okabe, Yokohama; Hisashi Mizumoto, Yokohama; Mitsunobu Isobe, Machida, all of (JP)

(73) Assignee: Hitachi, Ltd., Tokyo (JP)

( * ) Notice: Subject to any disclaimer, the term of this patent is extended or adjusted under 35 U.S.C. 154(b) by 59 days.

(21) Appl. No.: 09/593,955

(22) Filed: Jun. 15, 2000

(30) Foreign Application Priority Data

Jun. 17, 1999 (JP) .......................... 11-171185

(51) Int. Cl.[7] ............................... G01V 8/00
(52) U.S. Cl. ............................. 250/559.4; 250/208.1; 356/237.5
(58) Field of Search .................... 250/208.1, 559.4, 250/559.05, 559.39, 559.45, 559.46, 559.42, 559.43, 458.1, 459.1, 461.1; 356/394, 237.4, 237.5; 382/145, 149, 190, 195, 203

(56) References Cited

U.S. PATENT DOCUMENTS

| | | | | |
|---|---|---|---|---|
| 5,153,444 A | * | 10/1992 | Maeda et al. | 250/559.05 |
| 5,581,089 A | * | 12/1996 | Kohno | 250/461.1 |
| 5,649,022 A | * | 7/1997 | Maeda et al. | 382/141 |
| 5,717,518 A | | 2/1998 | Shafer et al. | |
| 5,774,222 A | * | 6/1998 | Maeda et al. | 356/394 |
| 6,087,673 A | | 7/2000 | Shishido et al. | |

FOREIGN PATENT DOCUMENTS

| | | | | |
|---|---|---|---|---|
| JP | 5-6928 | 1/1993 | | |
| JP | 5-264467 | 10/1993 | | |
| JP | 6-258239 | 9/1994 | | |
| JP | 6-324003 | 11/1994 | | |
| JP | 10-74812 | 3/1998 | | |
| JP | 10-318950 | * 4/1998 | ......... | G01N/23/225 |
| JP | 10-177139 | 6/1998 | | |

OTHER PUBLICATIONS

*Patent Abstracts of Japan*, English abstract of Japanese reference 10–318950 published on Dec. 4, 1998.

* cited by examiner

*Primary Examiner*—Robert H. Kim
*Assistant Examiner*—G Kao
(74) *Attorney, Agent, or Firm*—Antonelli, Terry, Stout & Kraus, LLP

(57) ABSTRACT

An apparatus and/or a method for inspecting fine defects on a substrate having minute patterns formed thereon as a target of inspection by detecting an image thereof with fine pixel size, wherein high speed processing is needed for position alignment over a wide region which is expanded equivalently therewith while obtaining a video processing circuit having a small size, wherein a video signal equal to or less than 0.2 μm in pixel size is obtained by using an optical system of DUV (far-ultraviolet) light or a video detection system of an electron beam. For instance, a search region for detecting position gaps is set at ±4 pixels, while on one substrate are mounted a plurality of video processing circuits, each being constructed with an LSI which can perform processing of k channels, thereby realizing a high-speed video processing portion having a small size.

41 Claims, 12 Drawing Sheets

TDI IMAGE SENSOR OF FRONT SURFACE IRRADIATION TYPE

TDI IMAGE SENSOR OF REVERSE SURFACE IRRADIATION TYPE (TDI : Time Delay & Integration)

MICROSCOPIC DEFECT INSPECTION APPARATUS AND METHOD THEREOF, AS WELL AS POSITIONAL SHIFT CALCULATION CIRCUIT THEREFOR

BACKGROUND OF THE INVENTION

The present invention relates to a microscopic defect inspection apparatus and a method thereof, as well as a positional shift or gap calculation circuit therefor, for detecting or inspecting very fine defects, such as very fine or minute foreign substances or matters and/or pattern defects on a subject, for example on substrates, in particular, the substrate which has repetitive patterns thereon, such as a semiconductor wafer, a reticule with phase sifter and a TFT substrate.

Conventional arts relating to a method for inspecting defects on repetitive patterns were already known, for example, in Japanese Patent Laying-Open No. Hei 5-264467 (1993) (Conventional art 1), Japanese Patent Laying-open No. Hei 5-6928 (1993) (Conventional art 2) and Japanese Patent Laying-Open No. Hei 10-74812 (1998) (Conventional art 3).

In those conventional arts 1, 2 and 3, there are described inspection of defects on the repetitive patterns, by detecting the positional shift or gap between video picture inputted and picture delayed by a pitch of the repetitive pattern so as to compensate or correct it. In particular, according to the conventional art 2, in the pattern inspection of detecting two (2) pictures formed to be the same pattern, so as to be compared with after being adjusted in positions thereof, thereby to determine the defects at the portions being inconsistent with each other on those video pictures, there is described that an amount of positional shifts or gaps on the pictures is detected at every predetermined time period, and that compensation or correction of those positional gaps is made dependent upon the amount of positional gaps up to the previous one.

Also, in the conventional art 3, there are described an inspection method for patterns as an object or target for inspection, wherein a video signal is detected from the repetitive patterns to be inspected, so as to produce a statistic video signal of the repetitive pattern therefrom, and then the defects or potential or pseudo-defects lying on the subject pattern are extracted by comparing this statistic video signal produced as a reference to the above-mentioned video signal detected after adjusting the positions thereof; and also an inspection method for the subject, i.e., the patterns to be inspected, wherein the video signal is detected from the repetitive patterns to be inspected, so as to produce a statistic information indicated by a statistic amount of the repetitive pattern from the detection video signal, and then the defects or potential or pseudo-defects lying on the subject pattern are extracted by treating a decision process upon the difference on video, being obtained by adjusting in position and then comparing the video signals of the above-mentioned repetitive patterns with each other, upon the basis of criteria being obtainable from the produced statistic information mentioned above. Further, in the conventional art 3, there is also described that the patterns as the subject are inspected with using an electron pictures thereof.

Further, a conventional art relating to a video picture detection system with using ultraviolet rays is already known in Japanese Patent Laying-Open No. Hei 10-177139 (1998) (Conventional art 4). In this conventional art 4, it comprises correcting mechanisms for primary and higher dimensions on various kinds of aberrations, including aberrations in the longitudinal and horizontal directions of spectrum, spreading over a wide band region from the ultraviolet to far-ultraviolet in the effective wavelength thereof, and there is further described a wide band ultraviolet ray video system, apply both principles of reflection and refraction therein, having a focus lens group composed of a plurality of lenses for providing the high dimensional correction on the video distortion within the same spectrum band or the aberration which causes change of color due to the chromatic aberration, a field lens group having at least two (2) refraction characteristics being different to each other, and further a catadioptric group.

For detecting the defects, such as breaks or short-circuits of lines on the wiring patterns, the picture video must be detected on the patterns as the target for inspection. However, the wiring patterns on semiconductor devices or the like are in a tendency of minimization, and the resolution is short or high on the picture which is obtained through an optical microscope under a visual light rays, therefore it is impossible to analyze the fine or microscopic patterns, then there occurs a necessity of using an optical microscope with using far-ultraviolet ray and/or an electron microscope.

However, in the conventional art 4 mentioned in the above, no consideration was taken on an aspect of enabling detection of the defects and/or foreign substances or matters of the very fine or minute patterns, occurring on the substrate as the target of inspection, on which the patterns are formed.

Also, none of the conventional arts 1, 2 and 3 mentioned above makes consideration on an aspect of enabling to detect the video signal having a high resolution through the optical microscope with using the far-ultraviolet ray.

Further, in a case of using the optical microscope with using far-ultraviolet ray and/or the electron microscope, since there occurs a necessity of detecting the video signal while reducing the size of the pixels, the number of the pixels lying within an area or region to be searched for detection and correction of the position shifts or gaps is enlarged or extended in that instance, the scale of circuitry to execute the video processing for detection and corrections of the position gaps is increased up, and the time necessary for that video processing of detection of the position shift and so on, as well.

However, none of the conventional arts 1, 2 and 3 mentioned above pays consideration on an aspect of small-sizing the circuit scale for performing the video processing of detection and correction of the position shift, nor of shortening the video processing time necessary for detection of the position shift and so on, in particular in the case of using the optical microscope with far-ultraviolet ray and/or the electron microscope.

SUMMARY OF THE INVENTION

An object according to the present invention, for dissolving the problems mentioned above, is to provide a fine defect inspection apparatus and a method thereof, wherein video processing for detection and correction of the position shift can be conducted upon the video signal detected by using the optical microscope with far-ultraviolet ray and/or the electron microscope, in the enlarged search area or region in which the number of the pixels thereof is increased up, thereby being able to perform the inspection with high reliability, but without failing to detect the very fine true defects erroneously.

Also, other object according to the present invention is to provide a fine defect inspection apparatus and a method thereof, wherein the video processing for detection and correction of the position shift can be conducted upon the video signal detected by using the optical microscope with far-ultraviolet ray and/or the electron microscope, at a high speed with high throughput, but without increasing up the circuit scale, thereby being able to perform the inspection with high reliability, but without failing to detect the very fine true defects erroneously.

Also, further other object according to the present invention is to provide a fine defect inspection apparatus and a method thereof, wherein the video signal detected with a high resolving power can be obtained from the optical microscope with far-ultraviolet ray, at high speed and with high resolution, thereby being able to perform the inspection with high reliability and also with high speed, but without failing to detect the very fine true defects erroneously.

Moreover, further other object according to the present invention is to provide a position shift calculation circuit for realizing the detection of the position gaps within the enlarged search area or region in which the pixel number is increased up, with using a circuit for use in detection of the position shift.

For accomplishing the object(s) mentioned above, in accordance with the present invention, there is provided an apparatus for inspecting fine defects upon a surface of a sample, comprising: a video signal detection portion for outputting video signal corresponding to 0.2 $\mu$m or less than that, in pitch size upon picking up of an image of the sample; an A/D converter portion for outputting detection video data through A/D conversion of the video signal outputted from said video signal detection portion; a reference video production circuit portion for producing reference video data to be compared with the detection video data outputted from said A/D conversion portion; a position gap detection circuit portion for detecting position gaps between the detection video data outputted from said A/D converter portion and the reference video data outputted from said reference video production circuit portion, to perform correction thereof; and a comparison circuit portion for comparing the detection video data, being corrected in position gaps thereof within said position gap detection portion, with the reference video data, so as to obtain pseudo-defect point, thereby to output information relating to said pseudo-defect point, wherein said position gap detection circuit portion and said comparison circuit portion are constructed with a circuit element of large scaled integration (LSI).

Also, in accordance with the present invention, there is provided an apparatus for inspecting fine defects upon a surface of a sample, comprising: a video signal detection portion for outputting video signal in parallel through multi-channels upon picking up of an image of the sample; an A/D converter portion for outputting detection video data in parallel through A/D conversion of each of the multi-channel video signal outputted from said video signal detection portion in parallel; a reference video production circuit portion for producing reference video data for the multi-channels in parallel, to be compared with the multi-channel detection video data outputted from said A/D conversion portion in parallel; a position gap detection circuit portion for detecting position gaps between the multi-channel. detection video data outputted in parallel from said A/D converter portion and the multi-channel reference video data outputted in parallel from said reference video production circuit portion, to perform correction thereof; and a comparison circuit portion for executing comparison of the multi-channel detection video data, being corrected in position gaps thereof within said position gap detection portion, with the multi-channel reference video data, so as to obtain pseudo-defect point therefrom, and extraction of information relating to said pseudo-defect point, by parallel processing thereof over the multi-channels.

Further, in accordance with the present invention, there is provided a method for inspecting fine defects upon a surface of a sample, comprising the following the steps: outputting video signal corresponding to 0.2 $\mu$m or less than that, in pitch size upon picking up of an image of the sample; outputting detection video data through A/D conversion of said video signal outputted; producing reference video data to be compared with the detection video data outputted; detecting position gaps between the detection video data outputted from said A/D converter portion and the reference video data outputted, to perform correction thereof; and comparing the detection video data, being corrected in position gaps thereof with the reference video data, so as to obtain pseudo-defect point, thereby outputting information relating to said pseudo-defect point, wherein the correction by detecting the position gaps and the outputting the information relating to said pseudo-defect point by obtaining the pseudo-defect point are performed within a circuit element of large scaled integration (LSI).

Furthermore, in accordance with the present invention, there is provided a method for inspecting fine defects upon a surface of a sample, comprising the following steps of: outputting video signal in parallel through multi-channels upon picking up of an image of the sample; outputting detection video data in parallel through A/D conversion of each of said multi-channel video signal outputted in parallel; producing reference video data for the multi-channels to be compared with the multi-channel detection video data outputted in parallel, thereby outputting it in parallel; detecting position gaps between the multi-channel. detection video data outputted in parallel and the multi-channel reference video data outputted in parallel, thereby to perform correction thereof; and executing comparison of the multi-channel detection video data, being corrected in position gaps thereof within said position gap detection portion, with the multi-channel reference video data, so as to obtain pseudo-defect point therefrom, and extraction of information relating to said pseudo-defect point, by parallel processing thereof over the multi-channels.

As was explained in the above, according to the construction mentioned above, the video signal having pixel size equal or less than 0.2 $\mu$m is detected by the video signal detection portion from the substrate as the target of inspection, therefore it is possible to perform the inspection with high reliability, but without erroneously failing to detect very fine or minute true defects, such as very fine foreign substances and/or pattern defects, etc., on the very fine patterns (being from 0.3 $\mu$m to 0.2 $\mu$m or less than that).

Also, with the construction mentioned in the above, wherein the video signal detection portion is constructed so as to comprise an optical irradiation system for irradiating DUV light having wavelength equal or less than 400 nm upon the substrate as a target to be inspected, and an optical detection portion for receiving the reflection light from said substrate to convert it into the video signal, and an image sensor for receiving the light is formed from the TDI image sensor being able to receive the DUV light, therefore the video signal having high resolution can be detected upon the basis of the scattering light or the diffraction light from the very fine defects, being equal or less than 0.1 $\mu$m, as a result of this it is possible to perform the inspection with high reliability, but without erroneously failing to detect very fine or minute true defects, such as very fine foreign substances and/or pattern defects, etc.

Further, with the construction mentioned in the above, wherein the video processing, such as the position gap detection and the position gap correction, etc., are processed in parallel within the video processing portion, and further with obtaining high speed being equal or higher than 20 MHz for the video processing within the circuit (LSI) for performing the video processing, the position gap detection and the position gap correction, etc., over the search region which is expanded in the number of pixels when the pixel size is equal or less than 0.2 μm, can be executed at high speed without increasing in the scale of circuitry, and as a result of this it is possible to realize the inspection with high reliability, but without erroneously failing to detect the very fine or minute true defects and at high throughput, by means of the construction of apparatus being simplified therein.

Those and other objects, feature and advantages of the invention will be apparent from the following more particular description of preferred embodiments of the invention, as illustrated in the accompanying drawings.

DESCRIPTION OF PREFERRED EMBODIMENTS

Hereinafter, embodiments of a fine defect inspection apparatus and a method thereof, according to the present invention, will be fully explained by referring to the attached drawings. Namely, an object or a target of inspection, i.e., a substrate 1 to be inspected for fine, minute or microscopic defects thereon, includes, for example, wiring patterns or a circuit patterns which are formed on a semiconductor wafer as semiconductor devices. The patterns formed on such the semiconductor device or the like are in a tendency of minimization, therefore detection of video or picture at high resolution is necessary for detecting defects including foreign substances or matters on those more fine or minute patterns (i.e., from 0.3 μm to 0.2 μm or less).

For detecting the video or picture of high resolution by analyzing the optical image of the defects including the foreign substances or matters on the fine or microscopic patterns in an optical inspection apparatus, there is necessity of shortening wavelengths of illumination lights, i.e., the wavelengths thereof must be shorter than that of the visible light rays. The reason of this is because the shorter the wavelengths of the illumination lights, the higher the optical resolution thereof.

Figure 1:
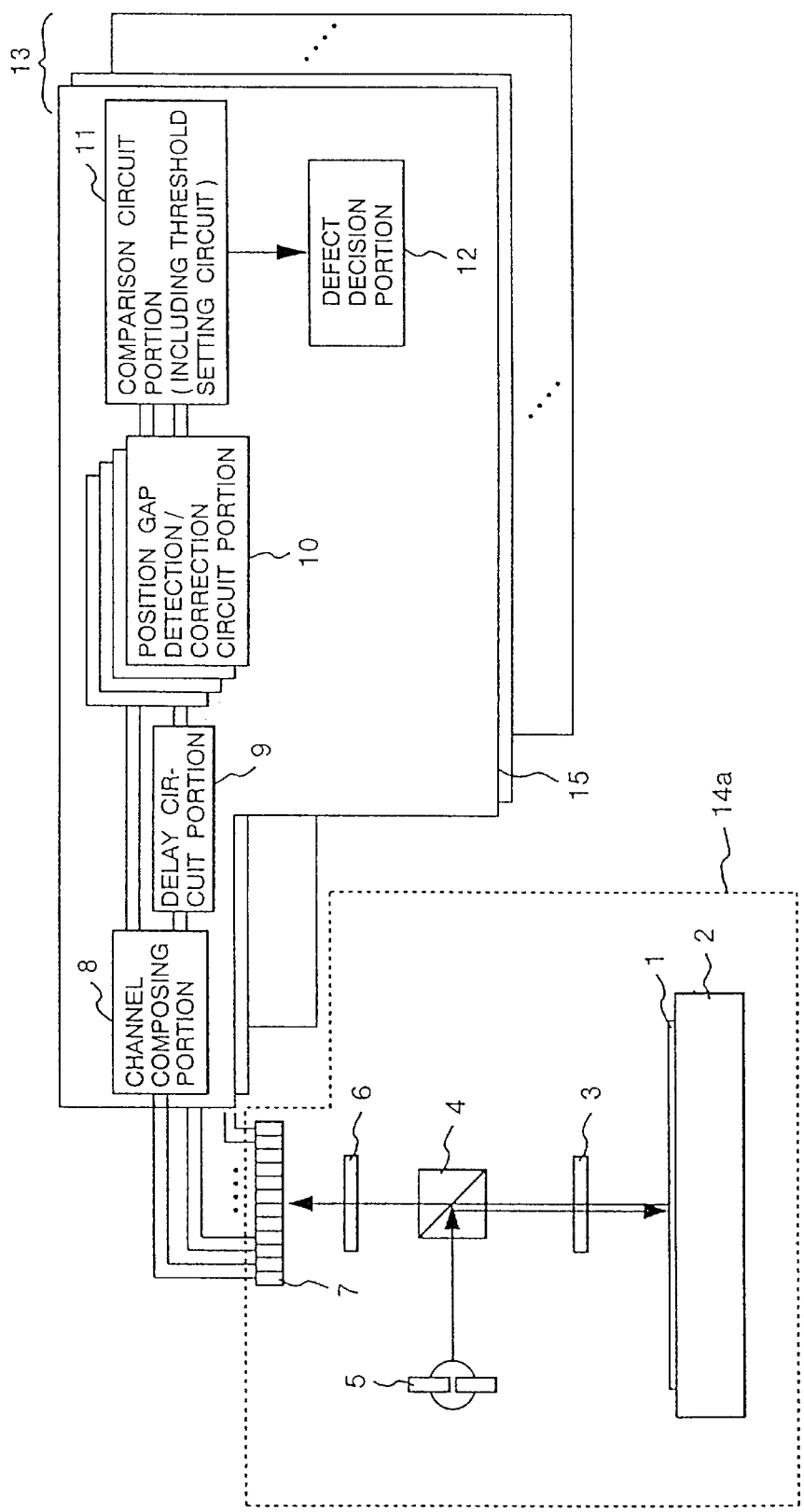
FIG. 1 is an outline view for showing the structure of a defect inspection apparatus of DUV optical type, as a first embodiment of a fine defect detection apparatus according to the present invention.

First, explanation will be given on an optical defect inspection apparatus, as a first embodiment of a fine defect inspection apparatus according to the present invention, by referring to FIG. 1. In this first embodiment, an optical system for illumination comprises an illumination source 5 constructed with a mercury-xenon lamp, etc., for conducting DUV (far-ultraviolet ray) illuminating, and a half-mirror 4 for reflecting the light emitted or irradiated from the illumination source 5 into the direction of the substrate 1, as the target of inspection, which is mounted on a stage 2, wherein the DUV light reflected by the half-mirror 4 penetrates through an objective lens 3, so as to fall an illumination light down to the substrate 1 as the target to be inspected. An optical system for detection comprises the objective lens 3 for taking in the light which is reflected, diffracted and scattered on the substrate 1 as the target of inspection, an interference filter 6 for DUV light for penetrating through the DUV light in the vicinity of 250 nm among the lights which are taken in by the objective lens 3 and penetrate through the half-mirror 4, an optical system for forming an enlarged image on an image sensor 7 by enlarging the DUV light obtained through the DUV light interference filter 6, and the image sensor 7 having a DUV quantum effect being about 10% or less than that, thereby being constructed so that a picture or video, which is detected on the substrate 1 as the target of inspection by the DUV light, can be obtained from the image sensor 7. In this manner, since the DUV light is short, such as being 400 nm or less than that in the wavelength, it is possible to obtain the picture or video of high resolution upon the basis of the scattered light or the diffraction light from the very fine defects (including the foreign substances or matters) being about 0.1 μm or less, with high resolving power.

As the illumination source 5 can also be used a DUV laser (for example, harmonic wave being higher than the third one of a YAG laser, KrF=248 nm of an excimer laser, ArF=193 nm of an excimer laser). In this instance, it is also possible to remove the DUV light interference filter 6 mentioned above in the above optical system for detection.

Also, in a case where it is necessary to make scanning by the DUV light, such as the DUV laser beam, upon a pupil of the objective lens 3 in a two (2) dimensional manner, it is enough to provide a pupil scanning illumination optical system for scanning the DUV illumination light, between the illumination light source 5 and the half-mirror 4 within the above-mentioned illumination optical system.

Further, in a case where the reflection light from a sample is detected with polarization thereof while illuminating the sample with polarized light, it is enough to provide an optical polarization control system for setting the polarization of the DUV illumination light, between the illumination light source 5 and the half-mirror 4 within the above-mentioned optical illumination system, and an optical polarization light detection system between the optical enlarged image forming system and the image sensor 7 within the optical detection system. And, the optical detection system may be constructed with a Fourier conversion lens, a space filter unit for shutting down the diffraction light from the patterns, which are formed on the substrate as the target of inspection with repetition at a small pitch, and another Fourier conversion lens, as is described, for example in Japanese Patent Laying-open No. Hei 6-258239 (1994) and Japanese Patent Laying-Open No. Hei 6-324003 (1994).

Furthermore, on the way of an optical path in the optical detection system is provided a half-mirror, thereby providing an automatic focusing system for fitting the focus of the objective lens upon the surface of the substrate 1 as the target of inspection through this half-mirror. Moreover, on the way of the optical path in the optical detection system is also provided another half-mirror, thereby enabling to observe the pupil position of the objective lens 3 through this half-mirror by an optical pupil observation system.

Figure 2A:
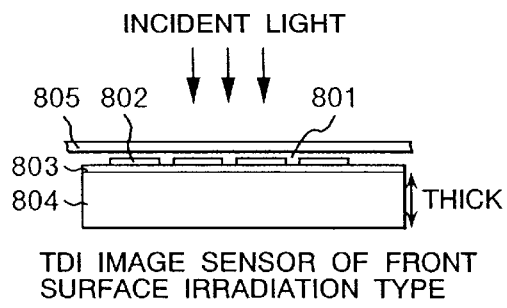
FIGS. 2(a) and (b) are views for showing an embodiment of a TDI image sensor according to the present invention.

By the way, since the DUV light source is used as the illumination light source 5, there is a necessity of using a sensor having high sensitivity for the DUV, as the image sensor 7 for detecting an optical image through the above-mentioned optical detection system. However, when using such a TDI (Time Delay Integration) image sensor of front surface irradiation type shown in FIG. 2(a), as the image sensor 7, since an incident light, penetrating through a cover glass 805 as well as an oxidation film (i.e., a $SiO_2$ film) 803 lying in a gate 801 between metal films 802, is incident upon a CCD formed on a Si substrate 804, the incident light having short wavelength is attenuated so that the sensor shows scarcely any sensitivity for the light of wavelength being less than 400 nm, therefore it cannot detect the DUV light as it is. Then, for obtaining enough or sufficient sensitivity for the DUV by the image sensor of surface irradiation type, there is a method of thinning the oxidation film 803 in the gate 801 so as to lessen the attenuation of the light of short wavelength. As an other method for that, an organic thin film coating (i.e., UV coating) is treated on the cover glass 805 so as to irradiate the visible light depending on the DUV light when it is incident upon, thereby detecting the DUV light by means of the image sensor having the sensitivity only for this visible light.

Figure 2B:
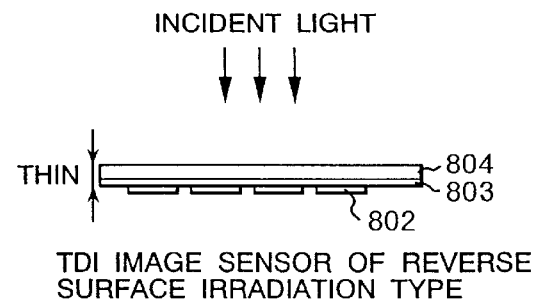

On the contrary to this, as shown in FIG. 2(b), using as the image sensor 7 the TDI sensor, but of reverse surface irradiation type, wherein the Si substrate 804 is made thin in thickness and the light is incident upon the reverse surface side of that thinned substrate, the light is incident upon from the reverse surface on which no gate structure is formed, so that the DUV quantum effect comes to be higher than about 10%, thereby obtaining a sensor having high quantum effect and large dynamic range, i.e., having the sensitivity for the light of wavelength less than 400 nm. Namely, with the TDI image sensor of reverse surface irradiation type, since the light is incident upon the reverse surface on which no gate structure is formed, it is possible to obtain the high quantum effect and the large dynamic range, so as to be sensitive even for the light of wavelength less than 400 nm, thereby enable to detect the DUV light.

As was mentioned in the above, with using such the image sensors, it is possible to detect the DUV light.

Also, by making the CCD image sensor 7 mentioned above of the TDI (Time Delay Integration) sensor having the DUV quantum effect larger than about 10%, it is possible to obtain the video of high dynamic range, and as a result of this, it is possible to obtain the video of high resolution. Also, by changing the output of the image sensor into a type of parallel outputs with multi-channels, it is possible to improve the throughput. With such the construction of the apparatus, it is possible to detect the image by the pixel size less than 0.2 $\mu$m (through conversion on the substrate 1, as the target of inspection).

Next, explanation will be given on a concrete embodiment of the video detection portion 14a. In a case where the image sensor 7 having a line rate higher than about 300 kHz and storage time less than about 5 $\mu$sec. is used for realizing high speed detection therewith, a large amount of light must be obtained for realizing brightness enabling the detection of defects. By making the image sensor 7 of the TDI image sensor (for example, the pixel size is 27 $\mu$m×27 $\mu$m) and of multi-stages of TDIs, it is possible to compensate for the shortage of the light amount. However, when making the number of the stages of TDIs large, it receives an influence of distortion on the stage (i.e., dynamic distortion) accompanying with travelling of the stage 2, largely. The number of the stages is variable from 96 stages to 512 stages depending upon an accuracy by the stages.

It is also necessary to make the light amount of the illumination large. Then, as the illumination light source 5 is used a mercury lamp of 35 mW, and the DUV illumination by means of the YAG laser of wavelength 255 nm or 248 nm is used.

As was explained in the above, with using the DUV illumination light source as the illumination light source 5 and the TDI image sensor having the sensitivity for the DUV illumination as the image sensor 7, it is possible to achieve detection of the video from the image sensor 7 of the video detection portion 14a, by the pixel size from 0.2 $\mu$m to 0.1 $\mu$m or less than that upon the substrate 1, as the target of inspection. Furthermore, when using the TDI image sensor of pixel size, for example 27 $\mu$m×27 $\mu$m, a magnification of the optical enlarged image forming system comes to be about from 135 times to 270 times or more than that.

Next, explanation will be given on the structure of the video processing portion 13 for detecting the defects from the video signal detected in the video detection portion 14a. The video output from the image sensor 7, being from 0.2 $\mu$m to 0.1 $\mu$m or less than that in the pixel size, which is produced from the TDI image sensor, is outputted in parallel via the multi-channels, then the video processing portion 13 is necessary for the number N of the channels. With increase of the number of the parallel connections, it is possible to achieve a high speed, however the scale of hardware for the video processing becomes large for it, therefore the apparatus is large-scaled.

Then, one of the objects according to the present invention is to realize the video processing portion 13 having a high speed and being small-sized in the circuit scale. Namely, the video processing portion 13 is constructed with plural pieces of video processing boards 15 so that the video processing can be executed in parallel. And, on each of the video processing boards 15 is installed a LSI (Large Scale Integrated Circuit) which is able to process the video data for the plural channels at the high speed inside. In particular, processing the video data for the plural channels in parallel, simultaneously, by means of the LSI installed on each of the image processing boards 15, and further by making the processing speed in that LSI as several times large as the processing speed for the board, it is possible to realize the video processing portion 13 being small in the circuit scale thereof.

By the way, when transferring a high speed clock signal being as several times high as 20 MHz on the video processing board 15 on which the LSI is installed, it easily receive an influence of noises, therefore it is difficult to realize it. Also, capability in selection of the parts mounted on the board as peripheral circuitry of the LSI, such as a memory, etc., comes to be small, therefore it is difficult to achieve the circuit construction with cheap.

Then, the video processing portion 13 is constructed with the video processing boards of a number of pieces of 1/k of the number N of the channels of the TDI image sensor 7, so as to enable the parallel and simultaneous processing of the video data. And, in each of the video processing boards 15 the clock speed inside the LSI mounted on the board is made as k times high as the clock speed of the signal on the board, thereby inputting the video signals (video data) fork channels to the LSI mounted on the board.

Further, in an input portion of the each video processing board 15 to the LSI, the video signals for k channels are composed to be that for one (1) channel, and the composed video signal for one (1) channel is video processed at the speed as k times high as in the LSI, thereby dividing the video signal for one (1) channel into those fork channels in the output portion for the LSI. Namely, in each of the video processing boards 15, after A/D conversion of the signals for the k pieces of neighboring channels (i.e., n pixels of the clock frequency f/line), which are outputted from the TDI image sensor 7 in parallel, into digital video signals (gradation values), they are converted into the signals which can be easily composed to be that for one (1) channel (i.e., kn pixels/line), for example, in the input portion of a position gap detection/correction circuit portion (or a position gap detection/adjusting circuit portion) 10, thereby to be outputted at the clock frequency f.

And, in a delay circuit portion 9 which is constructed with a shift memory, etc., being mounted on the each video processing board 15 the detection video signals (i.e., the gradation data) f(x,y) for n channels which are converted in a channel composing portion 8 are delayed by the time of the repetitive pattern thereof, so as to produce a reference video signal (i.e., the gradation data) g(x,y), thereby to be outputted at the clock frequency f. For example, in case of comparison by chips, the delay for the repetitive pattern is a unit of the chips, and in case of comparison by cells, that for the repetitive pattern is a unit the cells. Namely, in a case where memory cells are formed on the substrate 1 as the target of inspection, the comparison by the unit of cells is possible, however in a case where ordinary patterns are formed on it, the comparison is made by the unit of chips since they are formed thereon.

Next, in the input portion of the position gap detection/correction circuit portion 10, which is constructed with the LSI mounted on each of the video processing boards 15, the detection video signals f(x,y) for n channels converted in the channel composition portion 8 are composed to be the detection video signal for one (1) channel (kn pixels/line), as well as the reference video signals g(x,y) for k channels produced in the delay circuit portion 9 are composed to be the reference video signal for one (1) channel (kn pixels/line).

Following to the above, in the video processing circuit of the position gap detection/correction circuit portion 10, an amount Δδ(x,y) of difference in position (i.e., a position gap amount) between those two detection signals f(x,y) and g(x,y), each being composed for one (1) channel, is calculated out at the speed as k times faster as the clock frequency, so as to correct the position gaps between the both video signals depending upon that position gap amount Δδ(x,y), thereby executing the correction of the position gaps (i.e., position adjustment). Following to this, in the output portion of position gap detection/correction circuit portion 10, the detection video signal for one (1) channel corrected in the position gap (i.e., the position adjustment) is divided into f'(x,y) for k channels (n pixels/line), as well as the reference video signal for one (1) channel corrected in the position gap into g'(x,y), thereby to be outputted.

Next, in the input portion of a comparison circuit portion 11 which is constructed with the LSI mounted on each of the video processing boards 15, the detection video signal f'(x,y) for k channels (n pixels/line) corrected in position gaps which are outputted from the position gap detection/correction circuit portion 10, are composed into the detection video signal for one (1) channel (kn pixels/line), as well as, the reference video signal g'(x,y) for k channels (n pixels/line) corrected in position gaps are composed to be the reference video signal for one (1) channel (kn pixels/line). Following to this, in the video processing circuit of the comparison circuit portion 11, difference between the detection video signal f'(x,y) for one (1) channel (kn pixels/line) corrected in position gaps and the reference video signal g'(x,y) for one (1) channel (kn pixels/line) is taken at the speed as k times faster as the clock frequency f, so as to detect inconsistent portion as candidates of the defects (i.e., potential or pseudo-defects), thereby obtaining an information relating to those potential or pseudo-defects. Namely, while generating the video difference |f'(x,y)−g'(x,y)| at the speed as k times faster as the clock frequency f, points where the video difference |f'(x,y)−g'(x,y)| exceeds a threshold value Th are extracted as the potential or pseudo-defects at the speed as k times faster as the clock frequency f, thereby obtaining the information relating to the potential or pseudo-defects. The threshold value Th in this instance may be set in advance, manually, or the threshold value may be calculated for each video or for each point on the video, before or during the testing. With control of this threshold value, it is possible to adjust the sensibility of the defect inspection. Also, as the reason of detecting the potential or pseudo-defects, there may be a case of occurring erroneous detection because the difference is generated between both the video signals corrected in position gaps, even in a normal portion where no defect occurs. Following to this, in the output portion of the comparison circuit portion 1, the information relating to the points of the potential or pseudo-defects is divided into those for k channels (n pixels/line), and further the detection video signal for one (1) channel corrected in position gaps is also divided into f'(x,y) for k channels (n pixels/line) while the reference video signal for one (1) channel corrected in position gaps g'(x,y) is divided into for k channels (n pixels/line), thereby to be outputted.

Further, each of the position gap detection/correction circuit portion 10 and the comparison circuit portion 11, which are mounted on each of the video processing boards 15 constructing the video processing portion 13, is constructed with at least one LSI (video processing circuit). And, the clock frequency for processing in the position gap detection/correction circuit portion 10 and the comparison circuit portion 11 as the video processing circuit (LSI) is as k times faster as the clock frequency f (i.e., the clock frequency to the video processing board 15) which is outputted from the TDI image sensor in parallel, i.e., 20 MHz or higher than that. Accordingly, in an inside of the each video processing circuits (LSI) mounted on each of the video processing boards 15 the video data for k channels is processed at the high speed of the clock frequency, 20 MHz or more, then it is possible to make the circuit scale of each of the video processing boards 15 small-sized, and as a result of this, it is also possible to simplify the video processing portion 13 constructed with N/k pieces of the video processing boards 15, as a whole.

By the way, appropriately k is from 2 to 8. However, in the FIG. 1 is shown the case where k is equal to 2 (k=2), for example.

And, because the points of the potential or pseudo-defects which are detected in the comparison circuit portion 11 of each of the video processing boards includes erroneous or imaginary information, those points of the potential or pseudo-defects are decided to be the imaginary information or not, in a defect decision portion 12 constructed with the LSI. At least the detection video f'(x,y) for k channels including the potential or pseudo-defect points is transferred to the defect decision portion 12, and only true defects are extracted from the video, by executing an imaginary information decision process in detail, so as to delete the imaginary information therefrom. However, it is not necessarily needed that the defect decision portion 12 constructed from the LSI is mounted on each of the N/k pieces of video processing boards 15, but it may be provided for each plurality of video processing portions 15 or for the video processing portion 13 which is constructed with the N/k pieces of video processing boards 15.

Further, explanation will be given on the defect decision portion 12. In the comparison circuit portion (LSI) 11 mounted on each of the video processing boards 15, because the threshold value for comparison results is set to be lower, for the purpose of preventing from overlook of the defects, the extracted points of the potential or pseudo-defects includes the imaginary information, due to the influences of unevenness in the brightness, which may be caused by delicate difference in the shape of the patterns and difference in the film thickness. Then, countermeasure for that imaginary information is worked out in the defect decision portion 12. Namely, in the defect decision portion 12, when the potential or pseudo-defect point is detected, the detection video data f'(x,y) including the potential or pseudo-defect point is reserved, and then decision is made on whether it is the imaginary one or the true defect by using the detection video data f'(x,y) reserved. The decision of imaginary information is conducted after completing the inspection or during the inspection. In a case where the decision is made after completing the inspection, the decision may be made manually through recognition by eyes, however if the potential or pseudo-defect points are large in the number thereof, also there may be a method wherein they are selected by an automatic defect classifying apparatus, so as to execute the defect decision with high efficiency. When trying to conduct the decision during the inspection, the imaginary information decision may be conducted, by conducting the inspecting in detail again by using the reserved video data of the potential or pseudo-defect points. When trying to conduct the decision through recognition by eyes after the inspection, it may be enough to have only the detection video data containing the potential or pseudo-defect points therein, however when trying to conduct the classification and the decision automatically, it may be difficult to perform the decision only by the video data of defects. Then, the video data of the potential or pseudo-defect points is reserved, together with the reference video data g'(x,y) to be compared with, as one set, when it is reserved, thereby achieving the decision easily.

Next, explanation will be given on first and second embodiments, by referring to FIGS. 3, 4 and 5, concretely, wherein, for example, the video signal for two (2) channels are composed to be the video signal for one (1) channel, in each of the video processing boards 15 according to the present invention, to be processed in the video processing circuit constructed with the LSI, and thereafter the video signal for one (1) channel is divided therefrom.

Namely, in the first and second embodiments, channels a and b are neighboring with and operate in parallel to each other, therefore the video data (i.e., each the detection video data and the reference video data) 61 of the channel a being A/D converted, and the video data (i.e., each the detection video data and the reference video data) 62 of the channel b being A/D converted are inputted at the frequency f, simultaneously.

Figure 3:
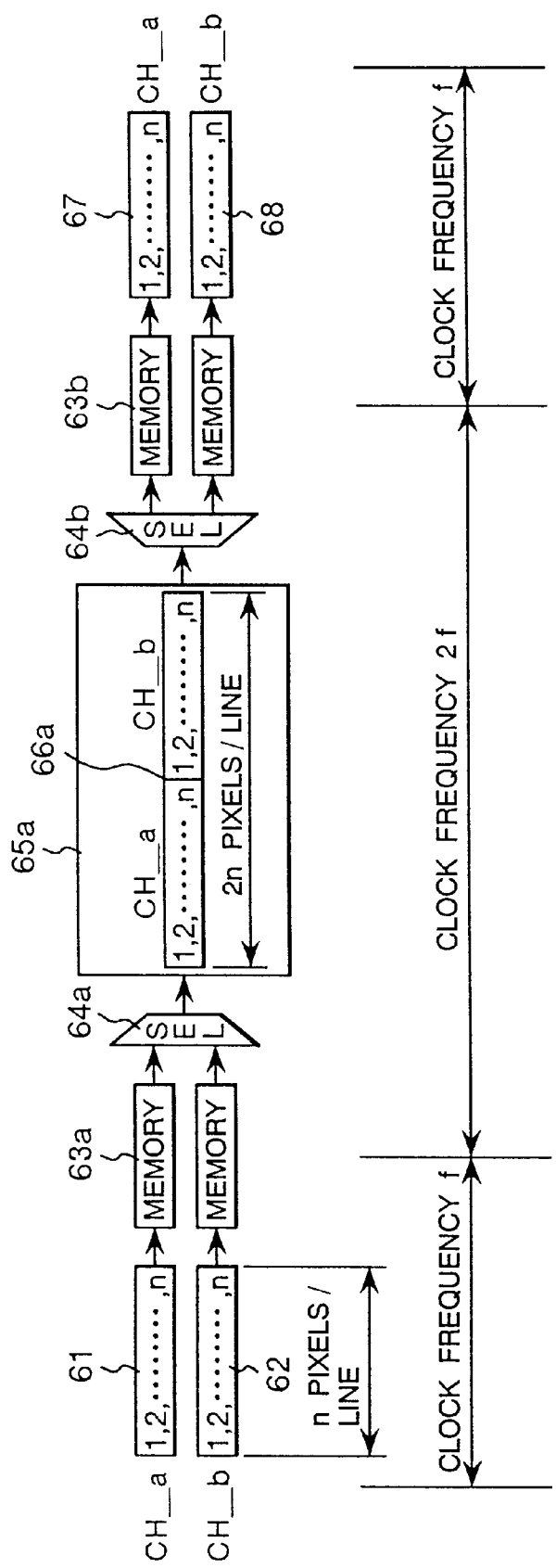
FIG. 3 is a view for explaining a first embodiment of a video processing circuit constructed with a LSI provided in a video processing portion, according to the present invention.

In case of the first embodiment, as shown in FIG. 3, each of the video data 61 and 62 is written into a respective memory 63a, once, and then each of the written video data 61 and 62 is read out from the memories 63a at frequency 2f, thereby to select the video data by a selector 64a so that the video data of the neighboring channels a and b are composed to be one for one (1) channel. For that purpose, inside a video processing circuit (LSI) 65a, each constructing the position gap detection/correction circuit portion 10 and the comparison circuit portion 11 therewith, the input video of n pixels/line is treated as video 66a of 2n pixels/line. At an output of the video processing circuit 65a, the video data processed is selected by a selector 64b and divided into video data corresponding to each of the channels a and b, thereby to be written into respective memories 63b. And, the processed video data which are written into the respective memories 63b are outputted at the clock frequency f as video data 67, 68.

Figure 4:
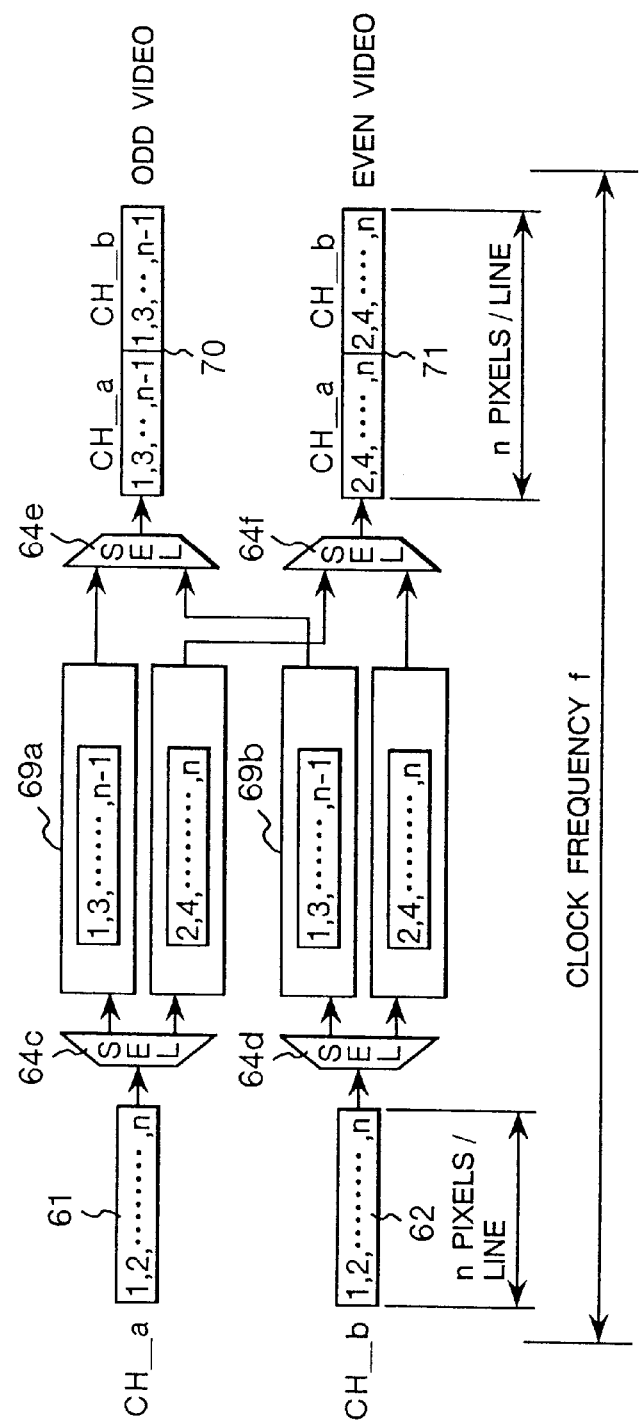
FIG. 4 is a view for explaining a circuit for converting an odd number video signals and an even number video signals for a plurality of channels, from video signals of those channels, which is provided in the video processing portion, according to the present invention.
Figure 5:
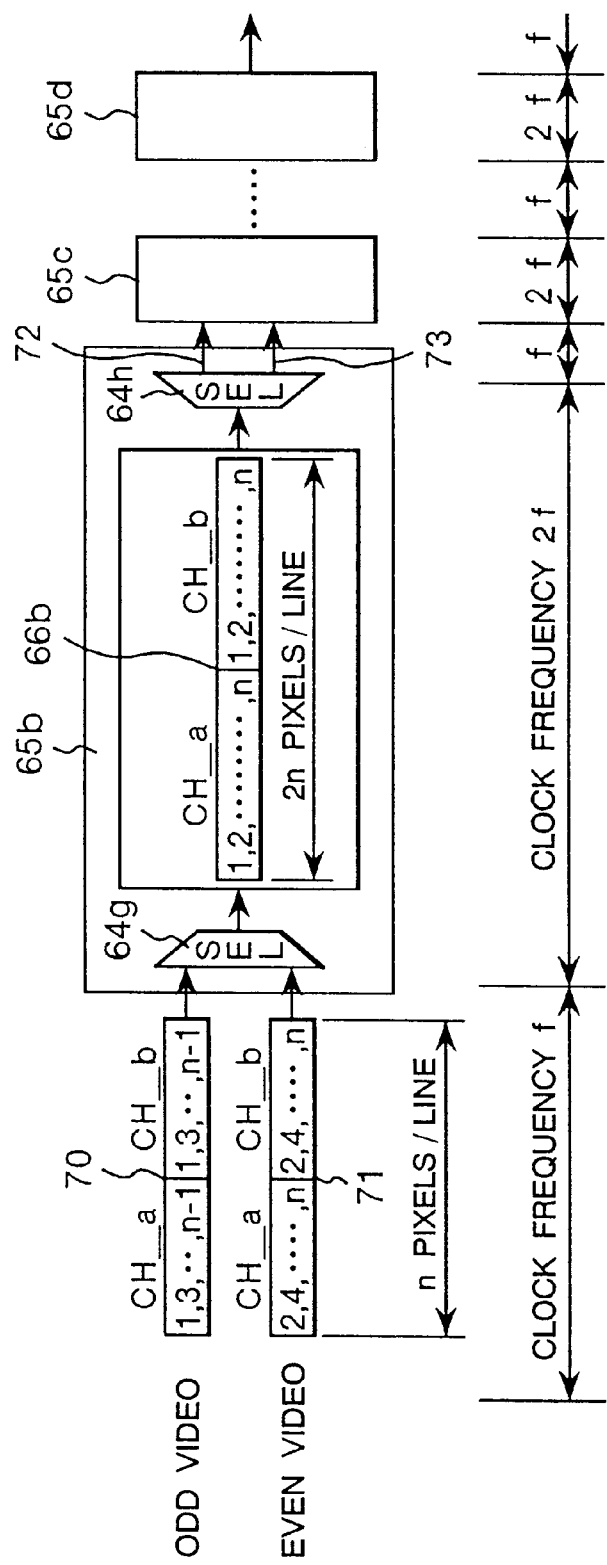
FIG. 5 is a view for explaining a second embodiment of the video processing circuit which is constructed with the LSI provided in the video processing portion, according to the present invention.

In case of the second embodiment, as shown in FIG. 4, with the video data 61 of the channel a which is inputted at the frequency f, it is first divided into odd number (ODD) pixels and even number (EVEN) pixels through a selector 64c, and then each is written into one of line memories (shift memories) 69a. At the same time, with the video data 62 of the channel b which is inputted at the frequency f, also it is first divided into odd number (ODD) pixels and even number (EVEN) pixels through a selector 64d, and then each is written into one of line memories (shift memories) 69b. And, the video data of the ODD pixels written into those line memories 69a and 69b are composed into an odd number video data 70 for two (2) channels of the ODD pixels (n pixels/line) through a selector 64e, while the video data of the EVEN pixels written into those line memories 69b and 69a are composed into an even number video data 71 for two (2) channels of the EVEN pixels (n pixels/line) through a selector 64f. The video data which was described up to here has the clock frequency f. Next, as shown in FIG. 5, at the input portion of the video processing circuit (LSI) 65b constructing the position gap detection/correction circuit portion 10, etc., i.e., at the selector 64g, the ODD video data and the EVEN video data are sampled alternately at the clock frequency 2f as two (2) times fast as the frequency f, so as to produce the video data (2n pixels/line) 66b after the composition of the signal for two (2) channels. In the video processing circuit (LSI) 65b, processings, such as the detection of position gaps and the correction of position gaps, are performed upon the basis of the video data for the two (2) channels a and b (being composed of the detection video data and the reference video data, each), thereafter the video data is sampled by the original clock frequency f in the selector 64h to be adjusted in the timing, and is divided into the ODD video data 72 for two (2) channels after processing of such as the correction on position gaps, etc., (being composed of the ODD detection video data and ODD reference video data, each) and the EVEN video data 73 for two (2) channels after processing such as the correction of position gaps, etc., (being composed of the EVEN detection video data and EVEN reference video data, each). Each of those ODD video data 72 for two (2) channels and EVEN video data 73 for two (2) channels, which are divided after processings thereof, is memorized, for example, into a line memory (not shown in the figures).

Next, in the video processing circuit (LSI) 65c constructing the comparison circuit portion 11, etc., in the same manner as in the video processing circuit (LSI) 65b at the clock frequency 2f as two (2) times fast, upon the basis of the video data for the two (2) channels a and b (being composed of the detection video data and the reference video data, each) which are processed with the position gap correction, there are conducted processings, such as, the extraction of difference video between the detection video data for two (2) channels a and b, and the extraction of the potential or pseudo-defects from the difference video by means of the threshold value are conducted, and thereafter, by extracting the potential or pseudo-defects therefrom and adding the position coordinate data of the potential or pseudo-defects, etc., the video data is divided into the ODD video data 72 for two (2) channels and the EVEN video data 73 for two (2) channels (being composed of the EVEN detection video data and EVEN reference video data, each), thereby to be outputted.

Lastly, in the video processing circuit (LSI) 65d constructing the defect decision portion 12, etc., in the same manner as in the video processing circuits (LSIs) 65b and 65c, upon the basis of the ODD video data 72 for two (2) channels (being composed of the ODD detection video data and ODD reference video data, each) and the EVEN video data 73 for two (2) channels (being composed of the EVEN detection video data and EVEN reference video data, each), which are extracted the potential or pseudo-defects therefrom and are added with the position coordinate data of the potential or pseudo-defects, etc., a characterizing amount of the potential or pseudo-defects is extracted to make a decision on whether it is the true defect or not, and is memorized into a memory (not shown in the figures) so as to be outputted as the information of the true defects (position information and the kinds of the defects).

As was explained in the above, according to the method of the second embodiment, once being divided into the ODD/EVEN pixels, the composition and the division thereof can be performed with ease at the input/output portions of each of the video processing circuits (LSIs) 65b, 65c, etc., and thereafter, there is no necessity of making the clock speed on the board as two (2) times fast as the frequency f, therefore it is effective for a case where the video processing portion as a whole is constructed with using the plural video processing LSIs.

Figure 6:
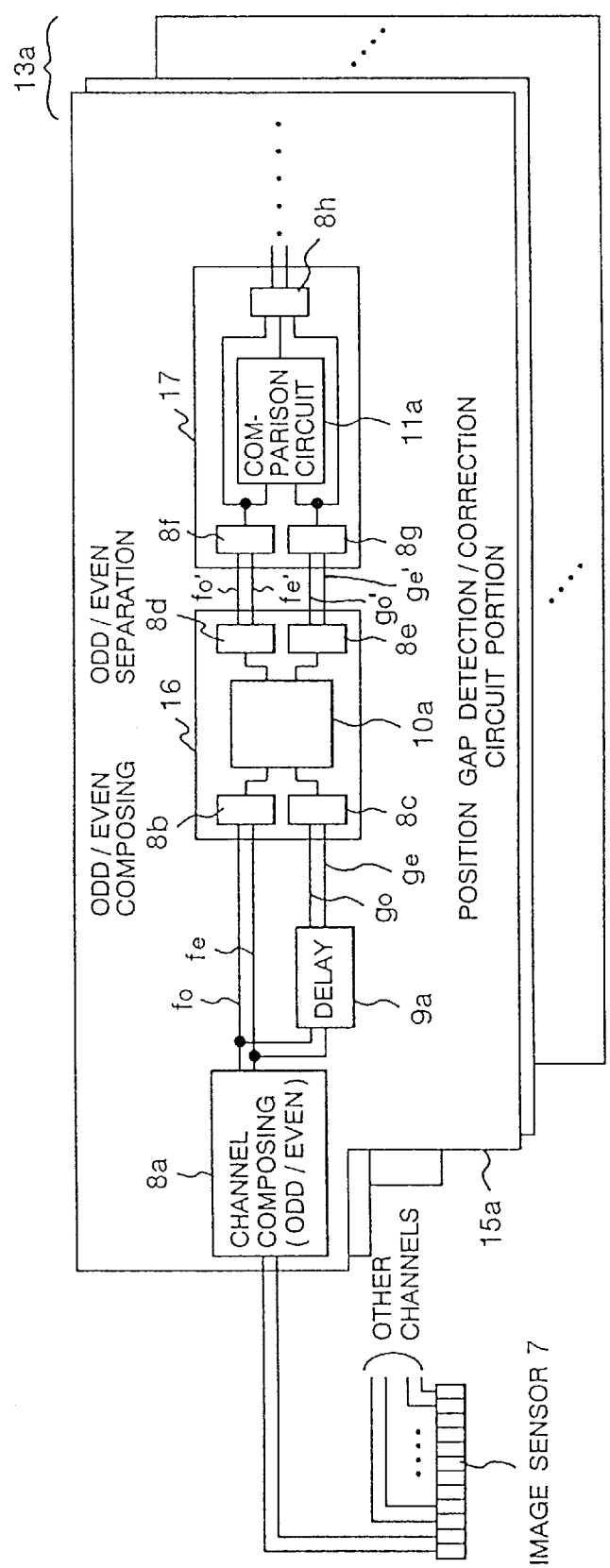
FIG. 6 is a view for showing the embodiment constructing the video processing portion according to the present invention, by installing the circuits shown in the FIGS. 4 and 5 on a substrate for each of the plural channels.

Explanation will be given on the plural pieces of the video processing boards 15a constructing the video processing portion 13a used in the second embodiment, in more details thereof, by referring to FIG. 6. Each of the video processing boards 15a comprises: a channel composition portion 8a for converting (or composing) the ODD detection video data (n pixels/line) of(x,y) (70) for two (2) channels and EVEN detection video data (n pixels/line) fe(x,y) (71) for two (2) channels after A/D conversion of the signal (n pixels/line of the clock frequency f) for the neighboring two (2) channels which are outputted from the TDI image sensor 7 in parallel; a delay circuit 9a for outputting the ODD reference video data (n pixels/line) go(x,y) (70) for two (2) channels and EVEN reference video data (n pixels/line) ge(x,y) (71) for two (2) channels by delaying the above-mentioned ODD detection video data (n pixels/line) of(x,y) (70) and EVEN detection video data (n pixels/line) fe(x,y) (71) by an amount of the repetitive pattern; a position gap detection/correction video processing circuit 16 which is constructed with one (1) LSI; a comparison video processing circuit 17 which is constructed with one (1) LSI; and a defect decision portion 12.

The above-mentioned channel composition portion 8a is so constructed as was mentioned in detail previously, as shown in the FIG. 4.

The position gap detection/correction video processing circuit 16 comprises an ODD/EVEN composition circuit portion 8b (64g) for converting into the composite detection video signal (2n pixels/line: clock frequency 2f) f(x,y) for one (1) channel, by composing the ODD pixel signal and the EVEN pixel signal on each of the detection video signals fo and fe which are obtained from the channel composition portion 8a; an ODD/EVEN composition circuit portion 8c (64g) for converting into the composite reference video signal (2n pixels/line: clock frequency 2f) g(x,y) for one (1) channel, by composing the ODD pixel signal and the EVEN pixel signal on each of the reference video signals go and ge which are obtained from the delay circuit 9a; a position gap detection/correction circuit portion 10a for performing the position gap detection/correction processes upon the basis of the composition detection video signal (2n pixels/line: clock frequency 2f) f(x,y) for one (1) channel and the composite reference video signal (2n pixels/line: clock frequency 2f) g(x,y) for one (1) channel; an ODD/EVEN separation circuit portion 8d (64h) for obtaining an ODD detection video signal fo' and an EVEN detection video signal fe' for two (2) channels, which are corrected in position gaps thereof, by separating the ODD pixel signal and the EVEN pixel signal from the composite detection video signal (2n pixels/line: clock frequency 2f) f'(x,y) for one (1) channel, which is corrected in position gaps in the position gap detection/correction circuit portion 10a; and an ODD/EVEN division circuit portion 8e (64h) for obtaining an ODD reference video signal go' and an EVEN reference video signal ge' for two (2) channels, which are corrected in position gaps thereof, by separating the ODD pixel signal and the EVEN pixel signal from the composition reference video signal (2n pixels/line: clock frequency 2f) g'(x,y) for one (1) channel, which is corrected in position gaps in the position gap detection/correction circuit portion 10a.

The comparison video processing circuit 17 comprises an ODD/EVEN composition circuit portion 8f for converting into the composite detection video signal (2n pixels/line: clock frequency 2f) f'(x,y) for one (1) channel, by composing the ODD pixel signal and the EVEN pixel signal on each of the detection video signals fo' and fe' which are obtained from the video processing circuit 15 and are corrected in position gaps thereof; an ODD/EVEN composition circuit portion 8g for converting into the composite reference video signal (2n pixels/line: clock frequency 2f) g'(x,y) for one (1) channel, by composing the ODD pixel signal and the EVEN pixel signal on each of the reference video signals go' and ge' which are obtained from the video processing circuit 15 and are corrected in position gaps thereof; a comparison circuit portion 11a of the clock frequency 2f, for comparing the detection video f'(x,y) corrected in position gaps to the reference video g'(x,y) so as to produce the difference video $|f'(x,y)-g'(x,y)|$ for two (2) channels, thereby extracting the points where the difference video $|f'(x,y)-g'(x,y)|$ exceeds the threshold value Th of the potential or pseudo-defects;

and a separation circuit portion 8*h* for separating into the detection video f'(x,y) and the reference video g'(x,y) for two (2) channels, to which are added the data (i.e., the position coordinate data) relating to the potential or pseudo-defects outputted from the comparison circuit portion 11*a*, to be outputted therefrom.

The defect decision portion 12, when needed to perform the processing at the clock frequency 2f, makes an analysis in detail upon the basis of at least the detection video signal f'(x,y) for each one channel, to which is added (or attached) the data relating to the potential or pseudo-defects obtained from the separation circuit portion 8*h* of the comparison video processing circuit 16, for obtaining the characteristic amounts of the potential or pseudo-defects (for example, coordinate of the center of gravity, a XY projection length (length), an area, a volume including gradation value, etc.), thereby to detect the true defects.

Next, explanation will be given on the position gap detection/correction circuit portion 10, in detail. By using the above-mentioned video detection portion 14*a*, it is possible to obtain the video of microscopic pixel size from the TDI image sensor 7, however when the pixel size is made small, the position gap detection/correction at high resolving power (i.e., wide range of the number of pixels) comes to be necessary in the position gap detection/correction circuit 10. Also, in a case where the dynamic distortion (distortion cannot be expected) occurs in the video detected upon the basis of a slight gap in traveling of the stage 2, the sensitivity in detection is deteriorated by the influence thereof. Also, when the number of field of view for inspecting all over the inspection area comes to be large within the substrate 1 as the target of inspection, a long inspection time is needed.

Then, for dissolving those problems, explanation will be given on a region of position gap detection/correction in the position gap detection/correction circuit 10. Though the TDI image sensor 7 of the video detection portion 14*a* conducts the inputs of video in synchronism with the stage 2 on which is mounted the substrate 1 as the target of inspection, since there is an error in traveling of the stage 2, the position gaps occur between the detection video f(x,y) and the reference video g(x,y). As was explained in the above, the position gap appear as the incoincidence or inconsistency in the comparison circuit portion 11 if it is, and it causes the imaginary information. Therefore, the position gaps are detected to be corrected in position in the position gap detection/correction circuit 10. If the area or region for searching the position gaps is narrow, the calculation of the position gaps can be processed or executed at high speed in the position gap detection/correction circuit 10, and the scale of it can be made small even if it is brought into hardware.

Figure 7:
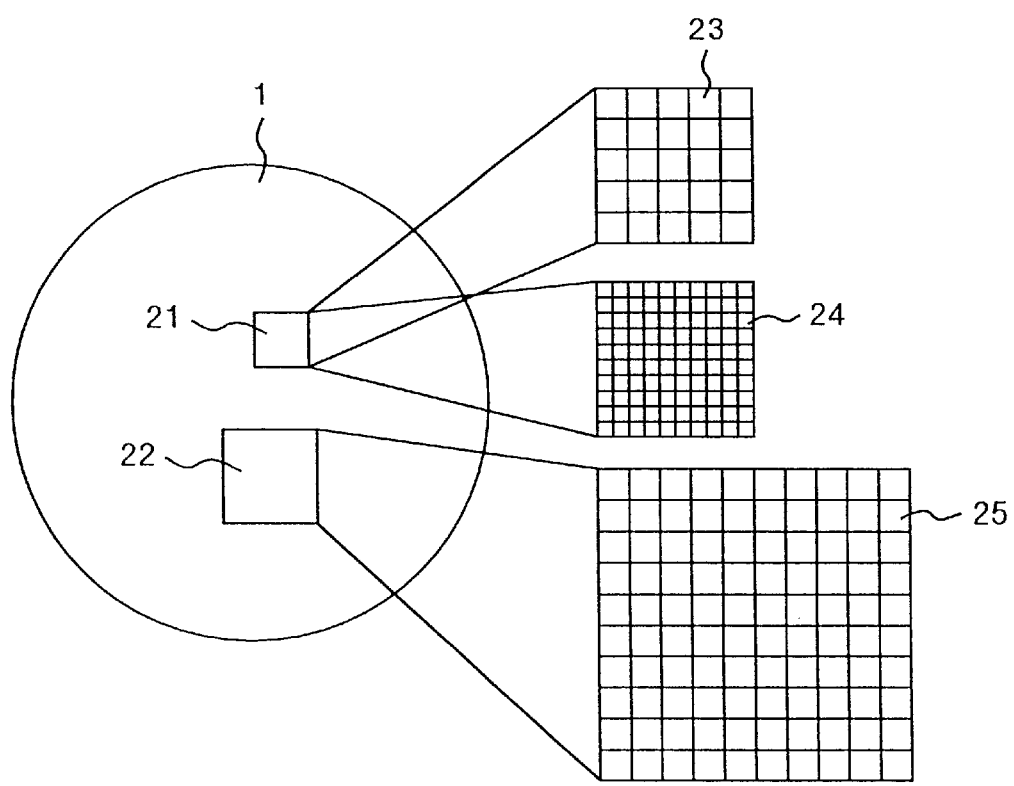
FIG. 7 is a view for explaining a relationship between a search area for searching position gaps and pixel size.

However, since this searching region for position gaps must be included within the dynamic maximum error caused due to the vibration or the like when traveling the stage 2, and/or the errors due to drift and so on of the mechanical and optical parts thereof, accompanying the change of temperature, and/or pitching error of the repetitive patterns formed on the substrate 1 as the target of inspection, it is determined upon dynamic accuracy of the stage 2 and the drifts of the mechanical and optical parts accompanying the change of temperature. Then, even trying to detect the DUV light by the TDI image sensor 7, so as to obtain high resolution, the search region for the position gaps comes to be the same when the drifts and so on of the mechanical and optical parts accompanying the dynamic accuracy and/or the change of temperature of the stage 2 are same. For example, as is shown in FIG. 7, within the same search region 21, when the pixel size comes to be a half (½) of the pixel size indicated by a numeral reference 24 in the search region 23, the number of pixels indicated by 24 comes to be as four (4) times large as the number of the pixels indicated by 23. This means, since the number of pixels to be searched is equal to, as indicated by 25, when the search region comes to be as four (4) times large as that, as indicated by 22, to reduce the pixel size is equivalent to widen the search region. Therefore, if trying to reduce for achieving the pixel size from 0.2 μm to 0.1 μm or less than that, for the purpose of obtaining the video data of high resolution by detecting the DUV light through the TDI image sensor 7, there is a necessity of the position gap detection and the position gap correction with high resolving power, being equivalent to the wide region and at high speed.

Figure 8:
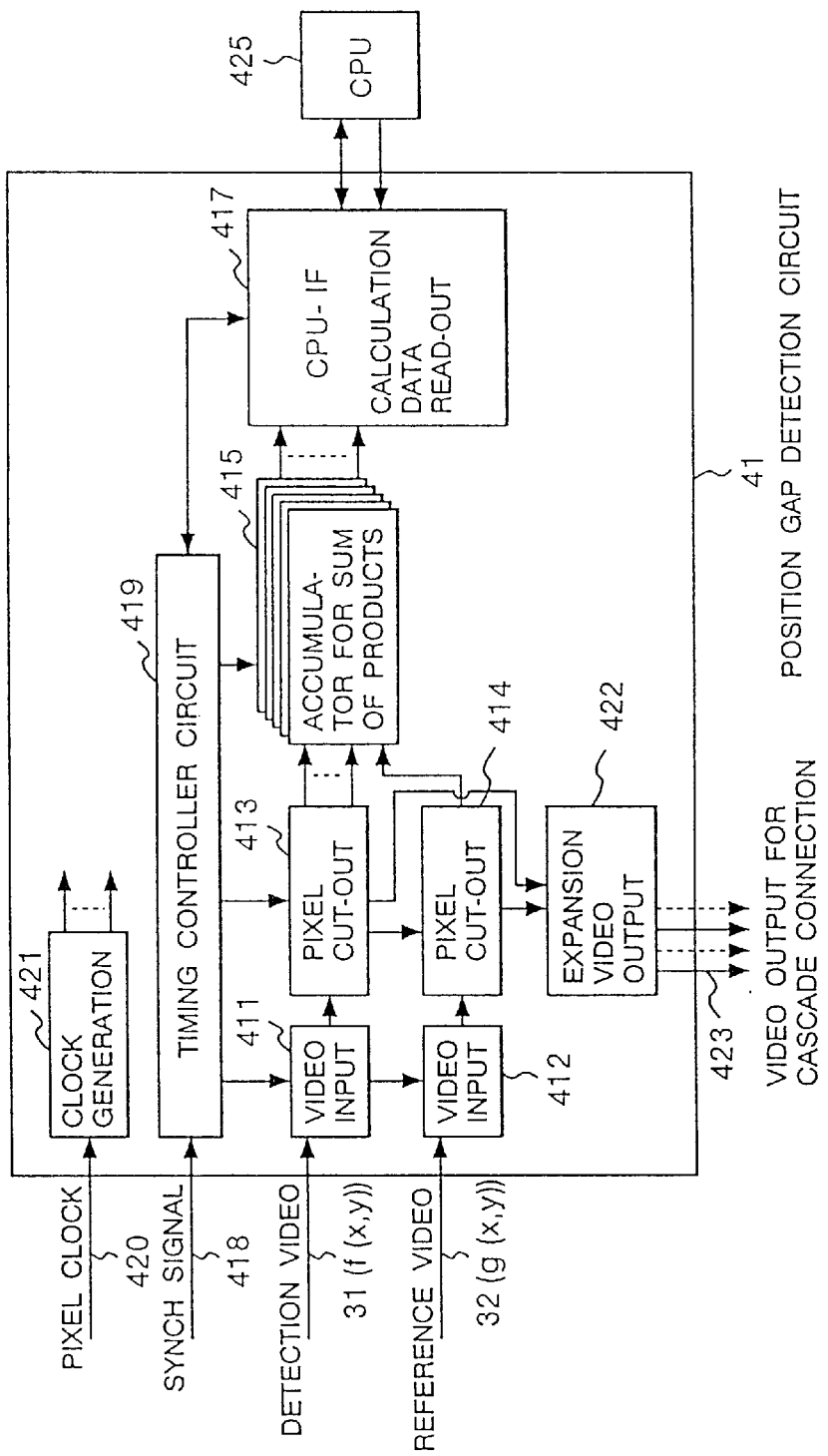
FIG. 8 is a view for showing an embodiment of a detecting circuit for detecting the position gaps according to the present invention.
Figure 9:
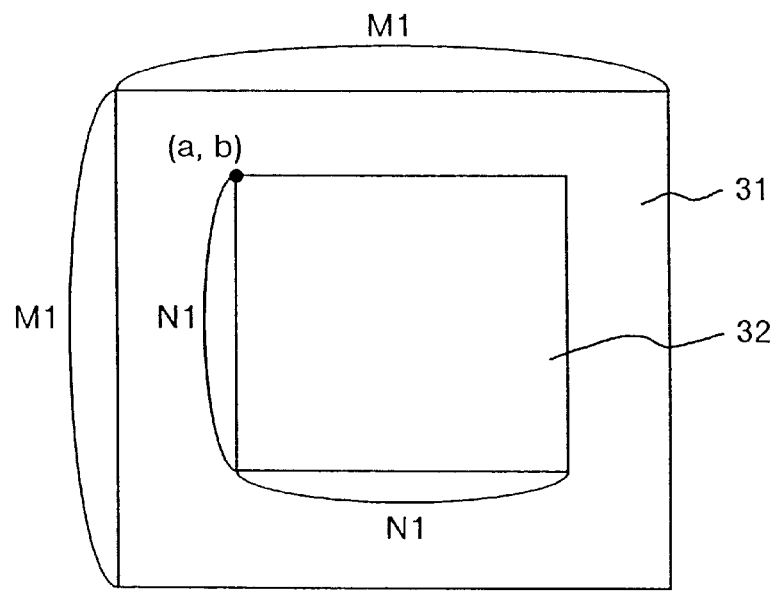
FIG. 9 is a view for explaining a template matching.

Next, explanation will be given on a position gap detection circuit for detecting the position gaps at high speed, by referring to FIGS. 8 and 9. Namely, for the position gap detection in the position gap detection circuit 41 is applied a template matching, as a general method therefor. This template matching is a methodology, wherein, with respect to the video of detection target (i.e., the detection video data) 31 (f(x,y)) which is inputted into a video input portion 411 to be cut out by a pixel cut-out portion 413, a standard video (i.e., the reference video data) 32 (g(x,y)) called by a template video which is inputted into a video input portion 412 to be cut out by a pixel cut-out portion 414 is moved or shifted in an accumulator 415 for sum of products, within the search region, thereby detecting a position where they coincide at the most in a calculation data read-out portion (CPU-IF) 417. In more detail, as shown in FIG. 9, the template video 32 of N1×N1 pixels is moved on the search region (M1−N1+1)×(M1−N1+1) within the detection video 31 of M1×M1 pixels, being larger than it, in the accumulator 415 for sum of products, wherein a degree of coincidence is calculated out in the calculation data read-out portion (CPU-IF) 417 at each position thereof. In this present embodiment, the search is made within the region of the video 31 of the inspection target by making the reference video (the standard video) as the template video 32, thereby to calculated out the position (a,b) where they are coincide at the most in position thereof. On the contrary, the search may be made within the region of the reference video 31 by making the detection video as the template video 32, thereby to calculated out the position (a,b) where they are coincide at the most in position thereof. Further, a reference numeral 419 is a timing controller circuit for taking timing for the video input portions 411 and 412, the video cut-out portions 413 and 414, the accumulator 415 for sum of products and the calculation data read-out portion 417, upon the basis of a synchronizing signal 418 inputted. A reference numeral 421 is a clock generator for generating a clock upon the basis of the video clock signal inputted, thereby performing processes within the video cut-out portions 413 and 414, the accumulator 415 for sum of products and the calculation data read-out portion 417.

As the template matching methods which can be applied into this present invention, there are listed up a residual sequential testing method, a normalized correlation, as well as a pyramid correlation. A method for alignment maybe selected depending upon the object of the testing apparatus.

In the residual sequential testing method, the position (a,b) of the template video 32 is calculated out at each potion in the search region, indicating a position gap amount ($\Delta\delta x, \Delta\delta y$) where the residual R(a,b) of the equation (Eq. 1) indicated below is at the minimum:

$$R(a, b) = \sum_{m1=0}^{N_1-1} \sum_{n1=0}^{N_1-1} |I_{(a,b)}(m1, n1) - T(m1, n1)| \quad \text{(Eq. 1)}$$

Here, (a,b) indicates the position at upper left-hand side of the template video 32 which is searched while being moved within the detection video 31, $I_{(a,b)}(m1,n1)$ the gradation value of a partial video of the detection video 31 in the (a,b) which is searched by while being moved, and T(m1,n1) the gradation value of the template 32. In this method, if the alignment is failed, the residual becomes large very quickly during when adding up sequentially in each pixel within the accumulator 415 for sum of products. Then, it is decided that the alignment is not good if the residual exceeds a certain threshold value, on the way of addition, thereby stopping the calculation so as to changed to calculation of next pixels. In this method, since the time for calculation can be shorten by stopping on the way thereof, therefore being suitable for the high speed inspection.

In the normalized correlation is calculated out the position at the upper left-hand side of the template video 32, indicating the position gap amount $(\Delta\delta x, \Delta\delta y)$ where C(a,b) of an equation (Eq. 2) indicated below comes up to the maximum:

$$C(a, b) = \sum_{m1=0}^{N_1-1} \sum_{n1=0}^{N_1-1} \frac{\{I_{(a,b)}(m1, n1) - Imean\}\{T(m1, n1) - Tmean\}}{\sqrt{I_{\delta ab} T_\delta}} \quad \text{(Eq. 2)}$$

However, Imean and Tmean in the above equation (Eq. 2) have relationships of equations (Eq. 3) indicated below:

$$Tmeans = (1/(N_t)^2) \sum_{m1=0}^{N_1-1} \sum_{n1=0}^{N_1-1} T(m1, n1) \quad \text{(Eq. 3)}$$

$$Imean = (1/(N_t)^2) \sum_{m1=0}^{N_1-1} \sum_{n1=0}^{N_1-1} I_{(a,b)}(m1, n1)$$

$$I_{\delta ab} = \sum_{m1=0}^{N_1-1} \sum_{n1=0}^{N_1-1} \{I_{(a,b)}(m1, n1) - Imean\}^2$$

$$I_\delta = \sum_{m1=0}^{N_1-1} \sum_{n1=0}^{N_1-1} \{T(m1, n1) - Tmean\}^2$$

In this method, since they are normalized, the influence upon the value of C(a,b) is small even if there is a difference in the brightness (i.e., in the gradation value) between two pieces of the detection video and the reference video. For example, if the video detection system 14 is constructed in an optical manner, though there may be cases where the brightness is different for each of the patterns due to the delicate difference of the thickness of the pattern as inspection target, however it is possible to achieve the alignment with high accuracy even for the video being different in the brightness thereof by using the normalized correlation.

In the pyramid correlation, not aligning or piling up with the video of high resolution from a beginning, but an operation of making a mean value of 2×2 pixels, for example, as the value for a layer upper by one is repeated, thereby producing the video which is reduced down in the resolution, sequentially. Next, after conducting rough alignment at the upper layers in which the resolution is reduced down, then gradually, an accurate alignment is performed in the lower layers in which the resolution is high. In this method, the search within the search region of each layer may be conducted by using either one of the residual sequential testing method, or the normalized correlation. It is enough to select the most suitable one depending upon specification of the inspection apparatus.

Figure 10:
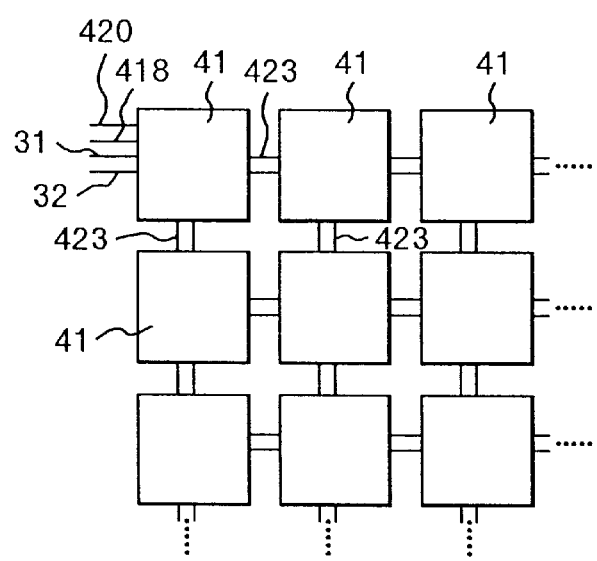
FIG. 10 is a view for explaining a cascade connection method of the position gap detecting circuit according to the present invention.

Next, explanation will be given of an embodiment, wherein the position gap detection is performed on the detection video data and the reference video data of high resolution, having a pixel size about from 0.2 μm to 0.1 μm or less, at high resolving power (wide range in the number of pixels) and high speed. With this embodiment, as shown in FIG. 10, the position gap detection circuits 41 are connected in cascade so as to enlarge the search region, thereby further enabling to detect the position gaps at the high speed. Namely, a plural number of the position gap detection circuits 41 are connected in vertical and horizontal directions so that they are wired by video outputs 423 which are outputted from expansion video output portions 422 as shown in FIG. 8. For connection thereof can be considered the method shown in FIG. 10. However, the pixel clock signal 420 and the synchronization signal 418 are inputted to each of the position gap detection circuits 41.

Figure 11A:
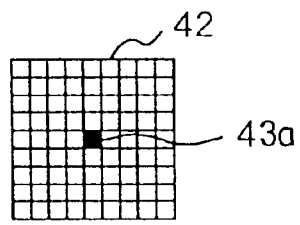
FIGS. 11(a), (b) and (c) are views for showing the search areas for the position gaps depending upon pixel groups, in particular in cases that the number of the detecting circuits of the position shift is one (1), four (4) and nine (9), respectively.
Figure 11B:
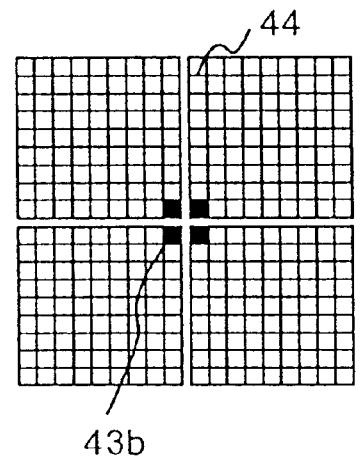
Figure 11C:
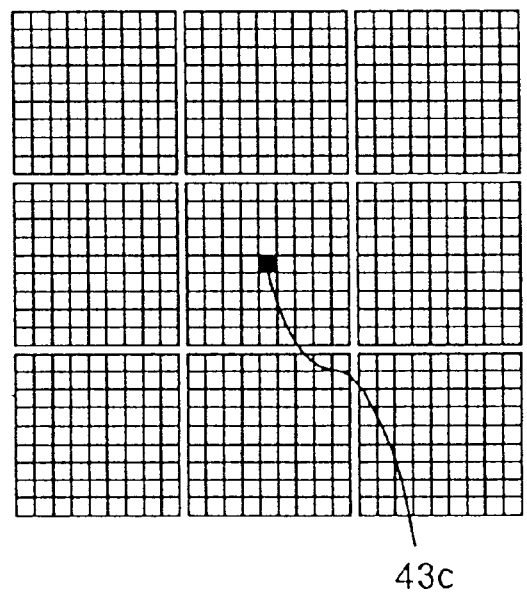

FIG. 11(a) shows a case where the position gap is detected within a region 42 of ±4 pixels to the detection video 31 around a standard position 43a of the template video (i.e., the reference video) 32, in one of the position gap detection circuits 41. FIG. 11(b) shows a case of the construction, where 2×2 pieces, i.e., totally four (4) pieces of the position gap detection circuits 41 are connected in cascade, wherein it is possible to detect the position gaps within the region of ±8 pixels to the detection video 31 around a standard position 43b of the template video (i.e., the reference video) 32, with making the neighboring pixels of each circuit as a duplicated region 44. FIG. 11(c) shows a case of the construction, where 3×3 pieces, i.e., totally nine (9) pieces of the position gap detection circuits 41 are connected in cascade, wherein it is possible to detect the position gaps within the region of ±12 pixels to the detection video 31 around a standard position 43c of the template video 32, with making the neighboring pixels of each circuit as a duplicated region 44. Further, in a case where the search region is widened or expanded, it is also possible to realize by increasing the number of the position gap detection circuits 41 connected. If there is no such necessity of making the search region for position gaps a square, it is also possible to set the search region for position gaps arbitrarily, by changing the number of connections in vertical and horizontal directions.

As was explained in the above, since the search region can be expanded by connecting the position gap detection circuits 41 in cascade, even when trying to obtain the high resolution by detecting the DUV light through the TDI image sensor 7, it is possible to realize the position gap detection and the position gap correction (position alignment) between the detection video data and the reference video data at the most suitable.

In the FIG. 11(a) is shown the example where the position gap search region of the one position gap detection circuit 41 is ±4 pixels, however if the position gap search region in the one circuit 41 is expanded or widen, it is apparent that the position gap detection and the position gap correction can be performed within the wide region even with a small number of the circuits connected in cascade.

Also, for bringing the above-mentioned position gap detection circuits 41 into the cascade connection, the outputs 423 relating to the detection video and the reference video for the cascade connection must be provided to the position gap detection circuits 41. As was shown in the FIG. 10, the outputs 423 relating to the detection video and the reference video are needed, in X and Y directions from each of the circuits 41, respectively. In a case where only one (1) direction is sufficient depending upon the search region, only an output in the x or Y direction is sufficient. In the case of the cascade connection, a CPU 425 extracts a statistic amount from the calculation data read-out portion 417 of each of circuits 41, so as to sum up the position gap results from each of the circuits 41, thereby calculating out the position gap amount as a total. Further, in a case of one position gap detection circuit 41, the position gap amount can be calculated in the calculation data read-out portion 417.

In particular, in a case of bringing the position gap detection circuits into the cascade connection within the position gap detection/correction circuit portion (LSI) 10 in each of the video processing board 13, there is a necessity of making the number k of the channels inputted into the each video processing board 13 very large. The reason of this lies in the difficulty of connecting the position gap detection portions to each other between the video processing boards 13. Also because, since the video is detected from the TDI image sensor 7 accompanying traveling of the stage, distortion occurs much in the video detected in the direction orthogonal to that of the stage traveling, then the cascade connection must be widen or extend in the search region directing orthogonal to that of the stage traveling.

Further, the position gap correction circuit is constructed with: a delay circuit (not shown in figures) for delaying the detection video data (gradation value) f(x,y) and the reference video data (gradation value) g(x,y) each, which are inputted into the position gap detection circuit 41, until the time when the position gap amount is calculated out in the position gap detection circuit 41; a memory (not shown in figures) for memorizing the detection video data f(x,y) and the reference video data g(x,y) which are delayed by that delay circuit; and an address selection circuit (not shown in figures) for obtaining the detection video data f'(x,y) and the reference video data g'(x,y), being treated with the position gap correction (position alignment) in the search region, through shifting an address to read out the detection video data f(x,y) from that memory by the position gap mount ($\Delta\delta x, \Delta\delta y$), which is calculated out upon the basis of the address for reading out the reference video data from the above-mentioned memory in the position gap search region, within the above-mentioned position gap detection circuit 41.

Figure 12:
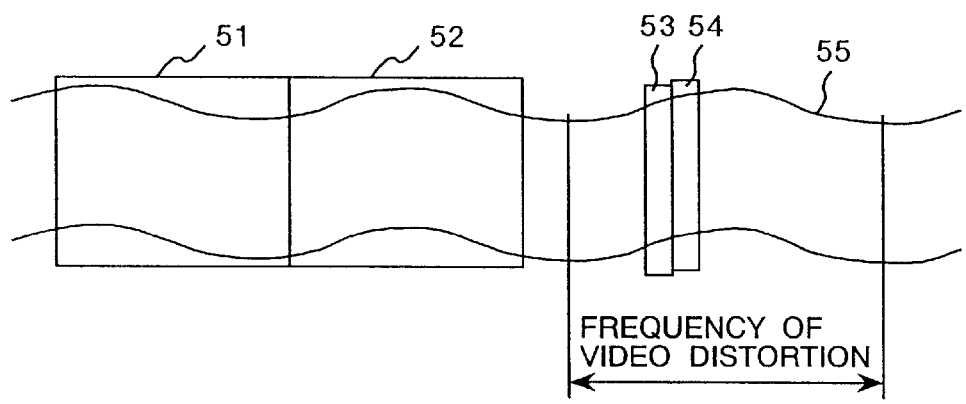
FIG. 12 is a view for explaining an influence of video distortion which is caused due to scanning on a stage.

Next, explanation will be given of the size of a video area as a unit for performing the position gap correction in the position gap detection/correction circuit portion 10. FIG. 12 shows a relationship between the dynamic distortion of the video detected by the TDI image sensor 7 and the size of the video area as the unit for performing the position gap correction. In a case where the video detection is performed in synchronism with the traveling of the stage, periodical video distortion 55 is produced in the video, because of unevenness in the traveling due to the vibration of the stage 2 or the like. In the case of producing the periodical video distortion in such a manner, if the size of the video area as the unit for performing the position gap correction is large, in spite of performance of the position gap correction between the detection video 51 and the reference video 52, a difference occurs in the shape of the pattern upon the basis of the distortion in the video, therefore the pattern comes to be erroneously detected to be the defect or the pseudo-defect, though it is in normal.

Then, for reducing the influence due to this distortion of video small, it is enough to bring the size of video area as the unit for performing the position gap correction to be smaller than the period of the distortion of video. If making it sufficiently smaller than the period of the distortion in this manner, it is possible to make the difference between the detection video 53 when being corrected in position gaps and the reference video 54 small, as a result, the influence of the distortion of video can be suppressed. In more detail, performing the position gap correction by the size of video area being less than one quarter (¼) of the period of video distortion, it is possible to remove the influence of the periodical video distortion.

However, it is enough that the position gap amount is detected between the detection video data and the reference video data, in the video area of the unit to be conducted with the position gap correction, therefore it is also possible to make the size of the video area, as the unit to be conducted with the position gap detection, smaller than the size of video area for performing the position gap correction.

As was explained in the above, a main factor of causing the position gap between the detection video data and the reference video data lies in the accuracy within the mechanisms of the stage or the like, the smaller the pixel size to be detected by the TDI sensor 7, the larger the number of pixels in the unit to be conducted with the position gap detection/correction, therefore there is a necessity of the position gap detection/correction circuit 10 at high speed.

Also, in the comparison circuit portion 11, since the potential or pseudo-defect point is extracted by comparing the detection video data f'(x,y) of the small pixel size and the reference video data g'(x,y), on which are conducted the position gap correction, the high speed processing is required, in the same manner.

However, as was mentioned previously, with providing a plural number of video processing boards 13 for enabling parallel processing, as well as a high speed clock (the clock being equal or higher than 20 MHz) within the LSIs 10 and 11 mounted on each of the video processing boards 13, it is possible to realize inspection with high resolving power and at high speed, from the video signal having high resolution, which is obtained by detecting the DUV light through the TDI image sensor 7 having the pixel size about from 0.2 $\mu$m to 0.1 $\mu$m or less.

For achieving the inspection with such the high sensitivity, the video processing portion 13 requires video input of high dynamic range from the video detection portion 14a. The video detection portion 14a performs inputting into the video processing portion 13 at the high dynamic range, and for utilizing the dynamic range effectively, an input of high resolution (of 10 bits, 1,024 gradation, or higher than that) is required. Therefore, into the video processing circuits (LSIs) 10 and 11 which are mounted on the plural number of the video processing boards 15 constructing the video processing portion 13, a signal of 10 bits, 1,024 gradation, or higher is inputted. However, in each of the video processing circuits (LSIs), depending upon the performance necessary, the video processing is carried out by reducing the resolving power thereof, for example, down to 8 bits or lower than that, so as to be processed therein. For example, as the video for use in detection of position gaps, since not necessary to be one of high resolving power, the gap amount is calculated out by using one of low resolving power, being equal or lower than 8 bits. When correcting the position of video depending upon the gap amount calculated out, the correction of position is performed by using the video of high resolving power of 10 bits or more. With this, it is possible to achieve a scale-down of the position gap detection circuit, as well as of small-sizing of the apparatus. The other video processing circuits (LSIS) mounted on each of the video processing boards 15 are also constructed to perform the video processing with the minimum but necessary bit number.

However, it is apparent that the above-mentioned position gap detection/correction circuit portion 10 and the comparison circuit portion 11 can be also applied between the detection video signal and the reference video signal, even in a case where the signal is detected from the video detection portion with the large pixel size.

Figure 13:
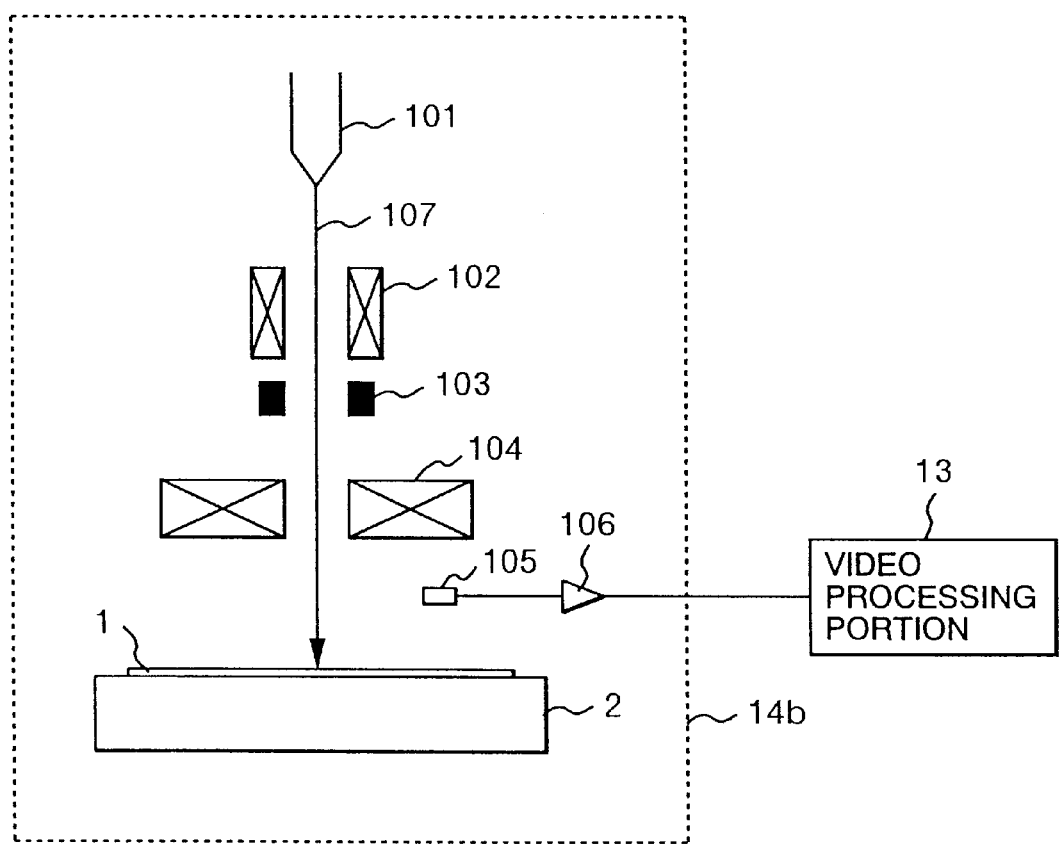
FIG. 13 is an outline view of the structure of an electron defect inspection as a second embodiment of the fine defect inspection apparatus, according to the present invention.

Next, explanation will be given on an electron defect inspection apparatus as a second embodiment of the fine defect inspection apparatus according to the present invention, by referring to FIG. 13. This second embodiment is constructed with a video detection portion 14b for obtaining an electron beam image of a scanned portion, depending upon the change of strength detected by electrons generated from the substrate 1 as the target of inspection, being scanned under irradiation of electron beam, and a video processing portion 13 performing pattern inspection by using the electron beam image obtained from that image detection portion 14b.

First, explanation will be given of the video detection portion 14b in the second embodiment. An electron beam 107 emitted from an electron gun 101, passing through a condenser lens 102 and an objective lens 104, is stopped to be an electron beam having diameter being about the pixel size on a sample surface. Upon irradiation of the electron beam 107, the substrate 1 as the target of inspection generates electrons therefrom. Detecting the electrons generated from the substrate 1 as the target of inspection by an electron detector 105 in synchronism with repetitive scanning by the electron beam 107 by means of a scanning deflector 103 and continuous movement of the substrate 1 as the target of inspection (i.e., the sample) on the stage 2, the electron beam image can be obtained in two-dimensional manner. The electron beam image generated from the substrate 1 as the target of inspection, after being caught by the electron detector 105 and amplified by an amplifier 106, is inputted into the video processing portion 13. This video processing portion 13 can be achieved with the same construction as the above-mentioned optical defect inspection apparatus. Namely, in the second embodiment, since the electron beam image can be obtained depending upon the repetitive scanning from the amplifier 106, therefore, by memorizing this electron beam image into a video memory once after being D/A converted so that a video signal can be taken out from this video memory corresponding to each channel, it is possible to input the video signal into each of the plural number of the video processing boards 15 constructing the video processing portion 13, in the same manner as in the above-mentioned optical defect inspection apparatus. In the present second embodiment, by reducing the electron beam diameter, the video of high resolution can be obtained, as well as the video having a pixel size of about 0.2 $\mu$m or less.

According to the present invention, upon the basis of the video signal which can detect the picture of very fine pattern pitch and/or the picture of very fine foreign substances, with high resolution and further with high resolving power by using the optical micro-scope with use of far-ultraviolet rays and/or the electron micro-scope, there can be obtained an effect of enabling inspection with high reliability, but without failing to detect very fine true defects.

Also, according to the present invention, upon the basis of the video signal which can detect the picture of very fine pattern pitch and/or the picture of very fine foreign substances, with high resolution and further with high resolving power by using the optical micro-scope with use of far-ultraviolet rays and/or the electron micro-scope, there also can be obtained an effect of enabling video processing of the position gap detection and position gap correction (position alignment), etc., between the detection video data and the reference video data having a small pixel size, and as a result of this, it is possible to perform the inspection with high throughput and high reliability, but without failing to detect very fine true defects.

Further, according to the present invention, upon the basis of the video signal which can detect the picture of very fine pattern pitch and/or the picture of very fine foreign substances, with high resolution and further with high resolving power by using the optical micro-scope with use of far-ultraviolet rays and/or the electron micro-scope, there also can be obtained an effect of obtaining a small-sizing of the processing circuits of performing the video processing for the position gap detection and the position gap correction (position alignment), etc., at high speed, and as a result of this, it is also possible to realize a small-sized inspection apparatus having high throughput therewith.

Furthermore, according to the present invention, in accordance with the construction of the video signal detecting portion, comprising an optical detection system for irradiating the DUV light of equal or less than 400 nm upon the substrate as the target of inspection, and an optical detection system for receiving reflection light from the substrate as the target of inspection to convert it into video signal, wherein the construction of the image sensor for receiving light is formed from the TDI image sensor enable to receive the DUV light, it is possible to detect the video signal having high resolution upon the basis of the scattering light and the diffraction light from the very fine defects being equal or less than 0.1 $\mu$m, and as a result of this, there can be obtained an effect that very fine true defects, such as very minute foreign substances and/or pattern detects, etc., can also be inspected with high reliability, but without erroneous detection thereof.

The invention may be embodied in other specific forms without departing from the spirit or essential characteristics thereof. The present embodiment is therefore to be considered in all aspects as illustrative and not restrictive, the scope of the invention being indicated by the appended claims rather than by the foregoing description and all changes come within the meaning and range of equivalency of the claims are therefore intended to be embraced therein.

What is claimed is:

1. An apparatus for inspecting defects of a sample, comprising:

a video signal detection portion for outputting a video signal in synchronism with a first frequency upon picking up an image of a sample;

an A/D converter portion for outputting detection video data through A/D conversion of the video signal outputted from the video signal detection portion;

a reference video production circuit portion for producing reference video data to be compared with the detection video data outputted from the A/D conversion portion;

a position gap detection circuit portion for detecting position gaps between the detection video data outputted from the A/D converter portion and the reference video data outputted from the reference video production circuit portion, to perform correction thereof in synchronism with a second frequency which is greater than the first frequency; and a comparison circuit portion for comparing the detection video data, being corrected in position gaps thereof within the position gap detection portion, with the reference video data in synchronism with the second frequency, so as to obtain a pseudo-defect point, thereby to output information relating to the pseudo-defect point.

2. An apparatus for inspecting defects of a sample according to claim 1, further comprising a defect decision circuit portion for deciding whether the pseudo-defect point is a true defect or not through detailed analysis.

3. An apparatus for inspecting defects of a sample according to claim 1, further comprising a DUV light irradiation means for irradiating the DUV light upon the sample;
wherein the video signal detection portion detects the image of the sample upon which the DUV light is irradiated by the DUV light irradiation means.

4. An apparatus for inspecting defects of a sample according to claim 3, wherein the video signal detection portion detects the image of the sample, upon which the DUV light is irradiated by the DUV light irradiation means, by using a TDI sensor.

5. An apparatus for inspecting defects of a sample according to claim 1, further comprising an electron beam irradiation means for irradiating an electron beam focused upon the sample;
wherein the video signal detection portion detects the image of the sample upon which the focused electron beam is irradiated by the electron beam irradiation means.

6. An apparatus for inspecting defects of a sample according to claim 1, wherein the comparison circuit portion further outputs the detection video data being corrected in position gaps thereof.

7. An apparatus for inspecting defects of a sample according to claim 1, wherein the comparison circuit portion calculates a position gap amount between the detection video data and the reference video data by means of a cascade matching.

8. An apparatus for inspecting defects of a sample, comprising:
a video signal detection portion for outputting a video signal in parallel through multi-channels in synchronism with a first frequency upon picking up an image of a sample;
an A/D converter portion for outputting detection video data in parallel through A/D conversion of each of the multi-channel video signal outputted from the video signal detection portion in parallel;
a reference video production circuit portion for producing reference video data for the multi-channels in parallel, to be compared with the multi-channel detection video data outputted from the A/D conversion portion in parallel;
a position gap detection circuit portion for detecting position gaps between the multi-channel detection video data outputted in parallel from the A/D converter portion and the multi-channel reference video data outputted in parallel from the reference video production circuit portion, and correcting the detected position gaps therebetween in synchronism with a second frequency which is greater than the first frequency; and
a comparison circuit portion for comparing the multi-channel detection video data with the multi-channel reference video data whose position gaps are corrected by the position gap detection circuit portion, so as to obtain a pseudo-defect point therefrom, and extracting information relating to the pseudo-defect point, by parallel processing thereof over the multi-channels.

9. An apparatus for inspecting defects of a sample according to claim 8, wherein the position gap detection circuit portion and the comparison circuit portion are constructed with a circuit element of large scaled integration (LSI).

10. An apparatus for inspecting defects of a sample according to claim 8, further comprising a DUV light irradiation means for irradiating the DUV light upon the sample;
wherein the video signal detection portion detects the image of the sample upon which the DUV light is irradiated by the DUV light irradiation means.

11. An apparatus for inspecting defects of a sample according to claim 10, wherein the video signal detection portion detects the image of the sample, upon which the DUV light is irradiated by the DUV light irradiation means, by using a TDI sensor.

12. An apparatus for inspecting defects of a sample according to claim 8, further comprising an electron beam irradiation means for irradiating an electron beam focused upon the sample;
wherein the video signal detection portion detects the image of the sample upon which the focused electron beam is irradiated by the electron beam irradiation means.

13. A method for inspecting defects of a sample, comprising the steps of:
outputting a video signal in synchronism with a first frequency upon picking up an image of a sample;
outputting detection video data through A/D conversion of the video signal outputted;
producing reference video data to be compared with the detection video data outputted;
detecting position gaps between the detection video data outputted from the A/D converter portion and the reference video data and correcting the detected position gaps therebetween in synchronism with a second frequency greater than the first frequency; and
comparing the detection video data with the reference video data whose position gaps are corrected in the detecting step, so as to obtain a pseudo-defect point, thereby outputting information relating to the pseudo-defect point.

14. A method for inspecting defects of a sample according to claim 13, further comprising the step of deciding whether the pseudo-defect point is a true defect or not through detailed analysis upon basis of the information relating to the pseudo-defect.

15. A method for inspecting defects of a sample according to claim 13, further comprising the steps of:
irradiating a DUV light upon the sample; and
detecting the image of the sample upon which the DUV light is irradiated.

16. A method for inspecting defects of a sample according to claim 15, further comprising the step of detecting the image of the sample, upon which the DUV light is irradiated, by using a TDI sensor.

17. A method for inspecting defects of a sample according to claim 13, further comprising the steps of:
irradiating an electron beam focused upon the sample; and
detecting the image of the sample upon which the focused electron beam is irradiated.

18. A method for inspecting defects of a sample according to claim 13, further comprising the step of calculating a position gap amount between the detection video data corrected in position gaps thereof and the reference video data by means of a cascade matching.

19. A method for inspecting defects of a sample, comprising the steps of:
   outputting a video signal in parallel through multi-channels in synchronism with a first frequency upon picking up an image of a sample;
   outputting detection video data in parallel through A/D conversion of each of the multi-channel video signal outputted in parallel;
   producing reference video data for the multi-channels to be compared with the multi-channel detection video data outputted in parallel, thereby outputting it in parallel;
   detecting position gaps between the multi-channel detection video data outputted in parallel and the multi-channel reference video data outputted in parallel, and correcting the detected position gaps therebetween in synchronism with a second frequency which is greater than the first frequency; and
   comparing the multi-channel detection video data with the multi-channel reference video data whose position gaps are corrected by the position gap detection circuit portion, so as to obtain a pseudo-defect point therefrom, and extracting information relating to the pseudo-defect point, by parallel processing thereof over the multi-channels.

20. A method for inspecting defects of a sample according to claim 19, wherein the detecting of position gaps to perform the correction and the extracting of the information relating to the pseudo-defect point through obtaining the pseudo-defect point are executed within a circuit element of large scaled integration (LSI).

21. A method for inspecting defects of a sample according to claim 19, further comprising the steps of:
   irradiating a DUV light upon the sample; and
   detecting the image of the sample upon which the DUV light is irradiated.

22. A method for inspecting defects of a sample according to claim 21, further comprising the step of detecting the image of the sample, upon which the DUV light is irradiated, by using a TDI sensor.

23. A method for inspecting defects of a sample according to claim 19, further comprising the steps of:
   irradiating an electron beam focused upon the sample; and
   detecting the image of the sample upon which the focused electron beam is irradiated.

24. An apparatus for inspecting defects of a sample, comprising:
   an image detecting unit which detects an image of a sample and outputs a plurality of video signals in parallel in synchronism with a first frequency;
   a reference data producing unit which produces reference data from the video signals outputted from the image detecting unit;
   a position gap correcting unit which corrects, in parallel, position gaps between the video signals outputted from the image detecting unit and the reference data produced by the reference data producing unit and outputs video signals subjected to position gap correction and reference data subjected to position gap correction;
   a defect candidate extracting unit which extracts defect candidates in synchronism with a second frequency which is greater than the first frequency by comparing the video signals subjected to position gap correction with the reference data subjected to position gap correction; and
   a defect judging unit which judges whether the defect candidates extracted by the defect candidate extracting unit are true defects.

25. An apparatus according to claim 24, wherein the image detecting unit includes an ultraviolet light source which illuminates the sample with an ultraviolet light.

26. An apparatus according to claim 25, wherein the image detecting unit further includes a reverse surface irradiation type TDI image sensor which detects an image of the sample illuminated with the ultraviolet light.

27. An apparatus according to claim 24, wherein the position gap correcting unit operates in synchronism with the second frequency.

28. An apparatus according to claim 24, wherein the second frequency is 2 to 8 times higher than the first frequency.

29. An apparatus according to claim 24, wherein the second frequency is greater than 20 MHz.

30. An apparatus according to claim 24, wherein the position gap correcting unit corrects the position gaps between the video signals outputted from the image detecting unit and the reference data produced by the reference data producing unit in each of a plurality of unit areas; and
   wherein each of the unit areas is smaller than one period of a video distortion in the video signals outputted from the image detecting unit.

31. An apparatus according to claim 24, wherein the defect judging unit judges whether the defect candidates are true defects asynchronously with the first frequency.

32. An apparatus according to claim 24, wherein the defect judging unit judges whether the defect candidates are true defects after the defect candidate extracting unit has finished extracting the defect candidates.

33. A method of inspecting defects of a sample, comprising the steps of:
   detecting an image of a sample and outputting a plurality of video signals in parallel in synchronism with a first frequency;
   producing reference data from the video signals outputted in the image detecting step;
   correcting, in parallel, position gaps between the video signals outputted in the image detecting step and the reference data produced in the reference data producing step and outputting video signals subjected to position gap correction and reference data subjected to position gap correction;
   extracting defect candidates in synchronism with a second frequency which is greater than the first frequency by comparing the video signals subjected to position gap correction with the reference data subjected to position gap correction; and
   judging whether the defect candidates extracted in the defect candidate extracting step are true defects.

34. A method according to claim 33, wherein the image detecting step includes the step of illuminating the sample with an ultraviolet light.

35. A method according to claim 34, wherein the image detecting step further includes the step of detecting an image of the sample illuminated with the ultraviolet light with a reverse surface irradiation type TDI sensor.

36. A method according to claim 33, wherein the position gap correcting step is performed in synchronism with the second frequency.

37. A method according to claim 33, wherein the second frequency is 2 to 8 times higher than the first frequency.

38. A method according to claim 33, wherein the second frequency is greater than 20 MHz.

39. A method according to claim 33, wherein in the position gap correcting step, the position gaps between the video signals outputted in the image detecting step and the reference data produced in the reference data producing step are corrected in each of a plurality of unit areas; and wherein each of the unit areas is smaller than one period of a video distortion in the video signals outputted in the image detecting step.

40. A method according to claim 33, wherein the step of judging whether the defect candidates extracted in the defect candidate extracting step are true defects is performed asynchronously with the first frequency.

41. A method according to claim 33, wherein the step of judging whether the defect candidates extracted in the defect candidate extracting step are true defects is performed after the defect candidate extracting step is finished.

\* \* \* \* \*